(12) United States Patent
Sel et al.

(10) Patent No.: US 8,119,789 B2
(45) Date of Patent: Feb. 21, 2012

(54) METHOD FOR THE PRODUCTION OF A CELL AND/OR TISSUE AND/OR DISEASE PHASE SPECIFIC MEDICAMENT

(75) Inventors: Serdar Sel, Marburg (DE); Harald Renz, Marburg-Cappel (DE)

(73) Assignee: Sterna Biologicals GmbH & Co. KG, Marburg (DE)

( * ) Notice: Subject to any disclaimer, the term of this patent is extended or adjusted under 35 U.S.C. 154(b) by 1334 days.

(21) Appl. No.: 10/574,560

(22) PCT Filed: Oct. 1, 2004

(86) PCT No.: PCT/DE2004/002197
§ 371 (c)(1),
(2), (4) Date: Feb. 1, 2007

(87) PCT Pub. No.: WO2005/033314
PCT Pub. Date: Apr. 14, 2005

(65) Prior Publication Data
US 2010/0249216 A1 Sep. 30, 2010

(30) Foreign Application Priority Data

Oct. 2, 2003 (DE) .................................. 103 46 487

(51) Int. Cl.
*C07H 21/04* (2006.01)
*A61K 48/00* (2006.01)
(52) U.S. Cl. .................... 536/24.5; 536/23.1; 514/44
(58) Field of Classification Search .................. None
See application file for complete search history.

(56) References Cited

U.S. PATENT DOCUMENTS 7,355,035 B1   4/2008   Atkins

FOREIGN PATENT DOCUMENTS

| WO | WO 00/09672 | * | 2/2000 |
| WO | WO 00/51621 | | 9/2000 |
| WO | WO 02/068637 A2 | * | 9/2000 |
| WO | WO 01/11023 | | 2/2001 |

OTHER PUBLICATIONS

Santoro S W et al; A general purpose RNA-cleaving . . . ; Nat. Acad. Sci., vol. 94, Apr. 1997; pp. 4262-4266.
Sun L Q et al; Catalytic nucleic acids . . . ; Pharma. Review; Williams & Wilkins Inc.; Sep. 2000; pp. 325-347.
Imagawa S et al; Negative regulation of the erythropoietin . . . ; Blood, W.B. Saunders; Feb. 1997; pp. 1430-1439.

* cited by examiner

*Primary Examiner* — Amy Bowman
(74) *Attorney, Agent, or Firm* — Jonathan Myers; Andrew Wilford

(57) ABSTRACT

The present invention relates to a method for producing of a cell and/or tissue and/or disease phase specific medicament against against chronic inflammatory diseases.
Disease, cell type, tissue and/or stage specific proteins and nucleic acids are identified with regard to their modified expression pattern and the corresponding nucleic acids are analyzed as possible attack targets for DNAzymes or siRNA. What follows is a design of active specific DNAzymes and siRNA which bind to the target sequence and cleave it such that a medicament against chronic inflammatory diseases and autoimmune diseases is provided.

7 Claims, 18 Drawing Sheets

Fig. 3

| Name | DNAzyme Sequenz |
|---|---|
| hgd1 | 5'-TCGGTCAGAggctagctacaacgaTGCGTTGCT-3' |
| hgd2 | 5'-GGCGTACGAggctagctacaacgaCTGCTCGGT-3' |
| hgd3 | 5'-GGCGGCGTAggctagctacaacgaACCTGCTC-3' |
| hgd4 | 5'-CTCGGGTCAggctagctacaacgaCTGGGTAGC-3' |
| hgd5 | 5'-TCCTCTGCAggctagctacaacgaCGGGGTCCT-3' |
| hgd6 | 5'-ACTCTGCAAggctagctacaacgaTCTGCGAGC-3' |
| hgd7 | 5'-GGGCGACGAggctagctacaacgaTCTGCAATT-3' |
| hgd8 | 5'-AAGGGGCGAggctagctacaacgaGACTCTGCA-3' |
| hgd9 | 5'-AAAACGGGAggctagctacaacgaCAGGTTGTA-3' |
| hgd10 | 5'-AGAATAAAAggctagctacaacgaGGGACCAGG-3' |
| hgd11 | 5'-ATGGCAGAAggctagctacaacgaAAAACGGGA-3' |
| hgd12 | 5'-AACTGGGTAggctagctacaacgaGGCAGAATA-3' |
| hgd13 | 5'-ATCCAAAAAggctagctacaacgaTGGGTATGG-3' |
| hgd14 | 5'-AGGGGAAGAggctagctacaacgaAAAAATCCA-3' |
| hgd15 | 5'-TTTTAAAAAggctagctacaacgaTATCTTGGA-3' |
| hgd16 | 5'-GTGGGGGGAggctagctacaacgaGGGAAGGCT-3' |
| hgd17 | 5'-GTTGAATGAggctagctacaacgaTTGCTTTCG-3' |
| hgd18 | 5'-GTCGTTGAAggctagctacaacgaGATTTGCTT-3' |
| hgd19 | 5'-GGCCCGGAAggctagctacaacgaCCGCGCGCG-3' |
| hgd20 | 5'-TCACCTCCAggctagctacaacgaGGCCTCGGC-3' |
| hgd21 | 5'-CCGCCGTCAggctagctacaacgaCTCCATGGC-3' |
| hgd22 | 5'-GGTGGCTCAggctagctacaacgaCCAGCGCGG-3' |
| hgd23 | 5'-CGTTGAGCAggctagctacaacgaGGCGGGGTG-3' |
| hgd24 | 5'-CCGCGTCCAggctagctacaacgaGTAGGAGTG-3' |
| hgd25 | 5'-CAGCGGGTAggctagctacaacgaTGCGCCGCG-3' |
| hgd26 | 5'-GCACATCCAggctagctacaacgaCTCCTCCGG-3' |
| hgd27 | 5'-AAAAGCACAggctagctacaacgaCCACCTCCT-3' |
| hgd28 | 5'-TAAAAAGCAggctagctacaacgaATCCACCTC-3' |
| hgd29 | 5'-GACCGTCGAggctagctacaacgaGTTAAAAAG-3' |
| hgd30 | 5'-TTGCCTTGAggctagctacaacgaCGTCGATGT-3' |
| hgd31 | 5'-AGGGCGGGAggctagctacaacgaGTGGTTGCC-3' |
| hgd32 | 5'-TGGCCCTGAggctagctacaacgaCGAGTTTCC-3' |
| hgd33 | 5'-ACCTCTGCAggctagctacaacgaCGTGGCCCT-3' |
| hgd34 | 5'-CGGAGGGTAggctagctacaacgaCTCTGCACC-3' |
| hgd35 | 5'-GGCGGCACAggctagctacaacgaCTGGCTCCC-3' |
| hgd36 | 5'-CGGGCGGCAggctagctacaacgaACCTGGCTC-3' |
| hgd37 | 5'-AGGGATCCAggctagctacaacgaGAAGCAGAG-3' |
| hgd38 | 5'-GGGTAGGGAggctagctacaacgaCCATGAAGC-3' |
| hgd39 | 5'-GGGCTGAGAggctagctacaacgaTCCAGGGGG-3' |
| hgd40 | 5'-GTGGATGGAggctagctacaacgaGTCTTGGAG-3' |
| hgd41 | 5'-CGTGGTGGAggctagctacaacgaGGACGTCTT-3' |
| hgd42 | 5'-GGGGGTAGAggctagctacaacgaGGAGAGGGG-3' |
| hgd43 | 5'-GGAGGAGGAggctagctacaacgaGAGGCCGGG-3' |
| hgd44 | 5'-GCCCCCCGAggctagctacaacgaAAGGAGGAG-3' |
| hgd45 | 5'-CCGGGGAGAggctagctacaacgaGTCCTTCGG-3' |
| hgd46 | 5'-GGACAGCGAggctagctacaacgaGGGTCCGGG-3' |
| hgd47 | 5'-TGGGGTGGAggctagctacaacgaAGCGATGGG-3' |
| hgd48 | 5'-CTTGAGGCAggctagctacaacgaTCTTTCTCG-3' |
| hgd49 | 5'-CACCTGGTAggctagctacaacgaTTGAGGCAC-3' |

Fig. 3 Cont.

| Name | DNAzyme Sequenz |
|---|---|
| hgd50 | 5'-GCAGGGGCAggctagctacaacgaCTGGTACTT-3' |
| hgd51 | 5'-CCAGCTTCAggctagctacaacgaGCTGTCGGG-3' |
| hgd52 | 5'-GTGGGACGAggctagctacaacgaTCCAGCTTC-3' |
| hgd53 | 5'-GGAGTGGGAggctagctacaacgaGACTCCAGC-3' |
| hgd54 | 5'-ATGCTGCCAggctagctacaacgaGGGAGTGGG-3' |
| hgd55 | 5'-GGGCGGTCAggctagctacaacgaGCTGCCACG-3' |
| hgd56 | 5'-GAGGCTCCAggctagctacaacgaCCAGGGCGG-3' |
| hgd57 | 5'-GTGGGTCGAggctagctacaacgaGAGGAGGCT-3' |
| hgd58 | 5'-AGGTGGTGAggctagctacaacgaGGGGTGGTG-3' |
| hgd59 | 5'-ACTCGGGCAggctagctacaacgaTAGGGCGG-3' |
| hgd60 | 5'-GGAGCTGTAggctagctacaacgaTCGGGCACG-3' |
| hgd61 | 5'-GGACTTGCAggctagctacaacgaCCGAAGCCG-3' |
| hgd62 | 5'-GGGCCTGGAggctagctacaacgaTTGCATCCG-3' |
| hgd63 | 5'-TGTGCTGGAggctagctacaacgaCGGGCCTTG-3' |
| hgd64 | 5'-GTTCACACAggctagctacaacgaTCCTGCCT-3' |
| hgd65 | 5'-CAGTTCACAggctagctacaacgaACTCCCTGC-3' |
| hgd66 | 5'-CACAGTTCAggctagctacaacgaACACTCCCT-3' |
| hgd67 | 5'-GTTGCCCCAggctagctacaacgaAGTTCACAC-3' |
| hgd68 | 5'-TCGCCGCCAggctagctacaacgaAGTGGGGTC-3' |
| hgd69 | 5'-CCCGTGCCAggctagctacaacgaCTCGCCGCC-3' |
| hgd70 | 5'-GGCGTTGCAggctagctacaacgaAGGTAGTGT-3' |

Fig. 4

Multiple Sequence Alignments GATA-3

```
Sequenz_1    1      GGCGCCGTCTTGATAC TTTCAGAAAGAATGCATTCCCTGTAAAAAAAAAAAAAAAAAT    60
Sequenz_2    ****   ----------------------------------------------------------   ****
Sequenz_3    1      GGCGCCGTCTTGATAC TTTCAGAAAGAATGCATTCCCTGTAAAAAAAAAAAAAAAAAT    60

Sequenz_1    61     -GAGAG CC GAGAG AGAGAGAAGAAGAGAGA GAGACGGAGGGAGAGCGAGACAGAGCG    119
Sequenz_2    ****   ----------------------------------------------------------   ****
Sequenz_3    61     TGAGAG CC GAGAG AGAGAGAAGAAGAGAGA GAGACGGAGGGAGAGCGAGACAGAGCG    120

Sequenz_1    120    AGCAACGCAATCTGAC CGAGCAGGTCGTACGCCGCCGCCTCCTCCTCCTCTCTGCTCTTC    179
Sequenz_2    ****   ----------------------------------------------------------   ****
Sequenz_3    121    AGCAACGCAATCTGAC CGAGCAGGTCGTACGCCGCCGCCTCCTCCTCCTCTCTGCTCTTC    180

Sequenz_1    180    GCTACCCAGGTGACCC GAGGAGGGACTCCGCCTCCGAGCGGCTGAGGACCCCGGTGCAGA    239
Sequenz_2    ****   ----------------------------------------------------------   ****
Sequenz_3    181    GCTACCCAGGTGACCC GAGGAGGGACTCCGCCTCCGAGCGGCTGAGGACCCCGGTGCAGA    240

Sequenz_1    240    GGAGCCTGGCTCGCAG AATTGCAGAGTCGTCGCCCCTTTTTACAACCTGGTCCCGTTTTA    299
Sequenz_2    ****   ----------------------------------------------------------   ****
Sequenz_3    241    GGAGCCTGGCTCGCAG AATTGCAGAGTCGTCGCCCCTTTTTACAACCTGGTCCCGTTTTA    300

Sequenz_1    300    TTCTGCC TACCCAGT TTTTGGATTTTTGTCTTCCCCTTCTTCTCTTTGCTAAACGACCC    359
Sequenz_2    ****   ----------------------------------------------------------   ****
Sequenz_3    301    TTCTGCC TACCCAGT TTTTGGATTTTTGTCTTCCCCTTCTTCTCTTTGCTAAACGACCC    360

Sequenz_1    360    CTCCAAGATAATTTTT AAAAAACCTTCTCCTTTGCTCACCTTTGCTTCCCAGCCTTCCCA    419
Sequenz_2    1      -------------------------------------------TCCCAGCCTTCCCA    14
Sequenz_3    361    CTCCAAGATAATTTTT AAAAAACCTTCTCCTTTGCTCACCTTTGCTTCCCAGCCTTCCCA    420

Sequenz_1    420    TCCCCCCACCGAAAGC AAATCATTCAACGACCCCCGACCCTCCGACGGCAGGAGCCCCCC    479
Sequenz_2    15     TCCCCCCACCGAAAGC AAATCATTCAACGACCCCCGACCCTCCGACGGCAGGAGCCCCCC    74
Sequenz_3    421    TCCCCCCACCGAAAGC AAATCATTCAACGACCCCCGACCCTCCGACGGCAGGAGCCCCCC    480

Sequenz_1    480    GACCTCCCAGGCGGAC CGCCCT CCTC CC CGCGCGGGTTCCGGGCCCGGCGAGAGGGC    539
Sequenz_2    75     GACCTCCCAGGCGGAC CGCCCT CC-C CC CGCGCGGGTTCCGGGCCCGGCGAGAGGGC    133
Sequenz_3    481    GACCTCCCAGGCGGAC CGCCCT CCTC CC CGCGCGGGTTCCGGGCCCGGCGAGAGGGC    540

Sequenz_1    540    GCGA ACAGCCGAGG CCATGGAGGTGACGGCGGACCAGCCGCGCTGGGTGAGCCACCAC    599
Sequenz_2    134    GCGA ACAGCCGAGG CCATGGAGGTGACGGCGGACCAGCCGCGCTGGGTGAGCCACCAC    193
Sequenz_3    541    GCGA ACAGCCGAGG CCATGGAGGTGACGGCGGACCAGCCGCGCTGGGTGAGCCACCAC    600

Sequenz_1    600    CACCCCGCCGTGCTCA ACGGGCAGCACCCGGACACGCACCACCCGGGCCTCAGCCACTCC    659
Sequenz_2    194    CACCCCGCCGTGCTCA ACGGGCAGCACCCGGACACGCACCACCCGGGCCTCAGCCACTCC    253
Sequenz_3    601    CACCCCGCCGTGCTCA ACGGGCAGCACCCGGACACGCACCACCCGGGCCTCAGCCACTCC    660

Sequenz_1    660    TACATGGACGCGGCGC AGTACCCGCTGCCGGAGGAGGTGGATGTGCTTTTTAACATCGAC    719
Sequenz_2    254    TACATGGACGCGGCGC AGTACCCGCTGCCGGAGGAGGTGGATGTGCTTTTTAACATCGAC    313
Sequenz_3    661    TACATGGACGCGGCGC AGTACCCGCTGCCGGAGGAGGTGGATGTGCTTTTTAACATCGAC    720

Sequenz_1    720    GGTCAAGGCAACCACG TCCCGCCCTACTACGGAAACTCGGTCAGGGCCACGGTGCAGAGG    779
Sequenz_2    314    GGTCAAGGCAACCACG TCCCGCCCTACTACGGAAACTCGGTCAGGGCCACGGTGCAGAGG    373
Sequenz_3    721    GGTCAAGGCAACCACG TCCCGCCCTACTACGGAAACTCGGTCAGGGCCACGGTGCAGAGG    780

Sequenz_1    780    TACCCTCCGACCCACC ACGGGAGCCAGGTGTGCCGCCCGCCTCTGCTTCATGGATCCCTA    839
Sequenz_2    374    TACCCTCCGACCCACC ACGGGAGCCAGGTGTGCCGCCCGCCTCTGCTTCATGGATCCCTA    433
Sequenz_3    781    TACCCTCCGACCCACC ACGGGAGCCAGGTGTGCCGCCCGCCTCTGCTTCATGGATCCCTA    840

Sequenz_1    840    CCCTGGCTGGACGGCG GCAAAGCCCTGGGCAGCCACCACACCGCCTCCCCCTGGAATCTC    899
Sequenz_2    434    CCCTGGCTGGACGGCG GCAAAGCCCTGGGCAGCCACCACACCGCCTCCCCCTGGAATCTC    493
Sequenz_3    841    CCCTGGCTGGACGGCG GCAAAGCCCTGGGCAGCCACCACACCGCCTCCCCCTGGAATCTC    900
                                                     hgd40
Sequenz_1    900    AGCCCCTT                      CACGGCTCCCCGGGGCCCCTCTCCGTCTACCCC    959
Sequenz_2    494    AGCCCCTTCTCCAAGA CGTCCATCCACCACGGCTCCCCGGGGCCCCTCTCCGTCTACCCC    553
Sequenz_3    901    AGCCCCTTCTCCAAGA CGTCCATCCACCACGGCTCCCCGGGGCCCCTCTCCGTCTACCCC    960

Sequenz_1    960    CCGGCCTCGTCCTCCT CCTTGTCGGGGGGCCACGCCAGCCCGCACCTCTTCACCTTCCCG    1019
Sequenz_2    554    CCGGCCTCGTCCTCCT CCTTGTCGGGGGGCCACGCCAGCCCGCACCTCTTCACCTTCCCG    613
Sequenz_3    961    CCGGCCTCGTCCTCCT CCTTGTCGGGGGGCCACGCCAGCCCGCACCTCTTCACCTTCCCG    1020

Sequenz_1    1020   CCCACCCCGCCGAAGG ACGTCTCCCCGGACCCATCGCTGTCCACCCCAGGCTCGGCCGGC    1079
Sequenz_2    614    CCCACCCCGCCGAAGG ACGTCTCCCCGGACCCATCGCTGTCCACCCCAGGCTCGGCCGGC    673
Sequenz_3    1021   CCCACCCCGCCGAAGG ACGTCTCCCCGGACCCATCGCTGTCCACCCCAGGCTCGGCCGGC    1080
```

Fig. 4 Cont.

```
Sequenz_1   1080   TCGGCCCGGCAGGACGAGAAAGAGTGCCTCAAGTACCAGGTGCCCCTGCCCGACAGCATG   1139
Sequenz_2    674   TCGGCCCGGCAGGACGAGAAAGAGTGCCTCAAGTACCAGGTGCCCCTGCCCGACAGCATG    733
Sequenz_3   1081   TCGGCCCGGCAGGACGAGAAAGAGTGCCTCAAGTACCAGGTGCCCCTGCCCGACAGCATG   1140

Sequenz_1   1140   AAGCTGGAGTCGTCCCACTCCCGTGGCAGCATGACCGCCCTGGGTGGAGCCTCCTCGTCG   1199
Sequenz_2    734   AAGCTGGAGTCGTCCCACTCCCGTGGCAGCATGACCGCCCTGGGTGGAGCCTCCTCGTCG    793
Sequenz_3   1141   AAGCTGGAGTCGTCCCACTCCCGTGGCAGCATGACCGCCCTGGGTGGAGCCTCCTCGTCG   1200

Sequenz_1   1200   ACCCACCACCCCATCACCACCTACCCGCCCTACGTGCCCGAGTACAGCTCCGGACTCTTC   1259
Sequenz_2    794   ACCCACCACCCCATCACCACCTACCCGCCCTACGTGCCCGAGTACAGCTCCGGACTCTTC    853
Sequenz_3   1201   ACCCACCACCCCATCACCACCTACCCGCCCTACGTGCCCGAGTACAGCTCCGGACTCTTC   1260

Sequenz_1   1260   CCCCCCAGCAGCCTGCTGGGCGGCTCCCCCACCGGCTTCGGATGCAAGTCCAGGCCCAAG   1319
Sequenz_2    854   CCCCCCAGCAGCCTGCTGGGCGGCTCCCCCACCGGCTTCGGATGCAAGTCCAGGCCCAAG    913
Sequenz_3   1261   CCCCCCAGCAGCCTGCTGGGCGGCTCCCCCACCGGCTTCGGATGCAAGTCCAGGCCCAAG   1320

Sequenz_1   1320   GCCCGGTCCAGCACAGAAGGCAGGGAGTGTGTGAACTGTGGGGCAACCTCGACCCCACTG   1379
Sequenz_2    914   GCCCGGTCCAGCACAG---GCAGGGAGTGTGTGAACTGTGGGGCAACCTCGACCCCACTG    970
Sequenz_3   1321   GCCCGGTCCAGCACAGAAGGCAGGGAGTGTGTGAACTGTGGGGCAACCTCGACCCCACTG   1380

Sequenz_1   1380   TGGCGGCGAGATGGCACGGGACACTACCTGTGCAACGCCTGCGGGCTCTATCACAAAATG   1439
Sequenz_2    971   TGGCGGCGAGATGGCACGGGACACTACCTGTGCAACGCCTGCGGGCTCTATCACAAAATG   1030
Sequenz_3   1381   TGGCGGCGAGATGGCACGGGACACTACCTGTGCAACGCCTGCGGGCTCTATCACAAAATG   1440

Sequenz_1   1440   AACGGACAGAACCGGCCCCTCATTAAGCCCAAGCGAAGGCTGTCTGCAGCCAGGAGAGCA   1499
Sequenz_2   1031   AACGGACAGAACCGGCCCCTCATTAAGCCCAAGCGAAGGCTGTCTGCAGCCAGGAGAGCA   1090
Sequenz_3   1441   AACGGACAGAACCGGCCCCTCATTAAGCCCAAGCGAAGGCTGTCTGCAGCCAGGAGAGCA   1500

Sequenz_1   1500   GGGACGTCCTGTGCGAACTGTCAGACCACCACAACCACACTCTGGAGGAGGAATGCCAAT   1559
Sequenz_2   1091   GGGACGTCCTGTGCGAACTGTCAGACCACCACAACCACACTCTGGAGGAGGAATGCCAAT   1150
Sequenz_3   1501   GGGACGTCCTGTGCGAACTGTCAGACCACCACAACCACACTCTGGAGGAGGAATGCCAAT   1560

Sequenz_1   1560   GGGGACCCTGTCTGCAATGCCTGTGGGCTCTACTACAAGCTTCACAATATTAACAGACCC   1619
Sequenz_2   1151   GGGGACCCTGTCTGCAATGCCTGTGGGCTCTACTACAAGCTTCACAATATTAACAGACCC   1210
Sequenz_3   1561   GGGGACCCTGTCTGCAATGCCTGTGGGCTCTACTACAAGCTTCACAATATTAACAGACCC   1620

Sequenz_1   1620   CTGACTATGAAGAAGGAAGGCATCCAGACCAGAAACCGAAAAATGTCTAGCAAATCCAAA   1679
Sequenz_2   1211   CTGACTATGAAGAAGGAAGGCATCCAGACCAGAAACCGAAAAATGTCTAGCAAATCCAAA   1270
Sequenz_3   1621   CTGACTATGAAGAAGGAAGGCATCCAGACCAGAAACCGAAAAATGTCTAGCAAATCCAAA   1680

Sequenz_1   1680   AAGTGCAAAAAAGTGCATGACTCACTGGAGGACTTCCCCAAGAACAGCTCGTTTAACCCG   1739
Sequenz_2   1271   AAGTGCAAAAAAGTGCATGACTCACTGGAGGACTTCCCCAAGAACAGCTCGTTTAACCCG   1330
Sequenz_3   1681   AAGTGCAAAAAAGTGCATGACTCACTGGAGGACTTCCCCAAGAACAGCTCGTTTAACCCG   1740

Sequenz_1   1740   GCCGCCCTCTCCAGACACATGTCCTCCCTGAGCCACATCTCGCCCTTCAGCCACCCCAGC   1799
Sequenz_2   1331   GCCGCCCTCTCCAGACACATGTCCTCCCTGAGCCACATCTCGCCCTTCAGCCACCCCAGC   1390
Sequenz_3   1741   GCCGCCCTCTCCAGACACATGTCCTCCCTGAGCCACATCTCGCCCTTCAGCCACCCCAGC   1800

Sequenz_1   1800   CACATGCTGACCACGCCCACGCCGATGCACCCGCCATCCAGCCTGTCCTTTGGACCACAC   1859
Sequenz_2   1391   CACATGCTGACCACGCCCACGCCGATGCACCCGCCATCCAGCCTGTCCTTTGGACCACAC   1450
Sequenz_3   1801   CACATGCTGACCACGCCCACGCCGATGCACCCGCCATCCAGCCTGTCCTTTGGACCACAC   1860

Sequenz_1   1860   CACCCCTCCAGCATGGTCACCGCCATGGGTTAGAGCCCTGCTCGATGCTCACAGGGCCCC   1919
Sequenz_2   1451   CACCCCTCCAGCATGGTCACCGCCATGGGTTAGAGCCCTGCTCGATGCTCACAGGGCCCC   1510
Sequenz_3   1861   CACCCCTCCAGCATGGTCACCGCCATGGGTTAGAGCCCTGCTCGATGCTCACAGGGCCCC   1920

Sequenz_1   1920   CAGCGAGAGTCCCTGCAGTCCCTTTCGACTTGCATTTTTGCAGGAGCAGTATCATGAAGC   1979
Sequenz_2   1511   CAGCGAGAGTCCCTGCAGTCCCTTTCGACTTGCATTTTTGCAGGAGCAGTATCATGAAGC   1570
Sequenz_3   1921   CAGCGAGAGTCCCTGCAGTCCCTTTCGACTTGCATTTTTGCAGGAGCAGTATCATGAAGC   1980

Sequenz_1   1980   CTAAACGCGATGGATATATGTTTTTGAAGGCAGAAAGCAAAATTATGTTTGCCACTTTGC   2039
Sequenz_2   1571   CTAAACGCGATGGATATATGTTTTTGAAGGCAGAAAGCAAAATTATGTTTGCCACTTTGC   1630
Sequenz_3   1981   CTAAACGCGATGGATATATGTTTTTGAAGGCAGAAAGCAAAATTATGTTTGCCACTTTGC   2040

Sequenz_1   2040   AAAGGAGCTCACTGTGGTGTCTGTGTTCCAACCACTGAATCTGGACCCCATCTGTGAATA   2099
Sequenz_2   1631   AAAGGAGCTCACTGTGGTGTCTGTGTTCCAACCACTGAATCTGGACCCCATCTGTGAATA   1690
Sequenz_3   2041   AAAGGAGCTCACTGTGGTGTCTGTGTTCCAACCACTGAATCTGGACCCCATCTGTGAATA   2100
```

Fig. 4 Cont.

```
Sequenz_1   2100   AGCCATTCTGACTCAT ATCCCCTATTTAACAGGGTCTCTAGTGCTGTGAAAAAAAAAA-T   2158
Sequenz_2   1691   AGCCATTCTGACTCAT ATCCCCTATTTAACAGGGTCTCTAGTGCTGTGAAAAAAAAAAAT   1750
Sequenz_3   2101   AGCCATTCTGACTCAT ATCCCCTATTTAACAGGGTCTCTAGTGCTGTGAAAAAAAAAAAT   2160

Sequenz_1   2159   GCTGAACATTGCATAT AACTTATATTGTAAGAAATACTGTACAATGACTTTATTGCATCT   2218
Sequenz_2   1751   GCTGAACATTGCATAT AACTTATATTGTAAGAAATACTGTACAATGACTTTATTGCATCT   1810
Sequenz_3   2161   GCTGAACATTGCATAT AACTTATATTGTAAGAAATACTGTACAATGACTTTATTGCATCT   2220

Sequenz_1   2219   GGGTAGCTGTAAGGCA TGAAGGATGCCAAGAAGTTTAAGGAATATGGGAGAAATAGTGTG   2278
Sequenz_2   1811   GGGTAGCTGTAAGGCA TGAAGGATGCCAAGAAGTTTAAGGAATATGGGAGAAATAGTGTG   1870
Sequenz_3   2221   GGGTAGCTGTAAGGCA TGAAGGATGCCAAGAAGTTTAAGGAATATGGGAGAAATAGTGTG   2280

Sequenz_1   2279   GAAATTAAGAAGAAAC TAGGTCTGATATTCAAATGGACAAACTGCCAGTTTTGTTTCCTT   2338
Sequenz_2   1871   GAAATTAAGAAGAAAC TAGGTCTGATATTCAAATGGACAAACTGCCAGTTTTGTTTCCTT   1930
Sequenz_3   2281   GAAATTAAGAAGAAAC TAGGTCTGATATTCAAATGGACAAACTGCCAGTTTTGTTTCCTT   2340

Sequenz_1   2339   TCACTGGCCACAGTTG TTTGATGCATTAAAAGAAAATAAAAAAAAGAAAAAAGAGAAAAG   2398
Sequenz_2   1931   TCACTGGCCACAGTTG TTTGATGCATTAAAAGAAAATAAAAAAAAGAAAAAAGAGAAAAG   1990
Sequenz_3   2341   TCACTGGCCACAGTTG TTTGATGCATTAAAAGAAAATAAAAAAAAGAAAAA-GAGAAAAG   2399

Sequenz_1   2399   A---------------- --------------------------------------------   2399
Sequenz_2   1991   AAAAAAAAAGAAAAAA GTTGTAGGCGAATCATTTGTTCAAAGCTGTTGGCCCTCTGCAAA   2050
Sequenz_3   2400   AAAAAAAAAGAAAAAA GTTGTAGGCGAATCATTTGTTCAAAGCTGTTGGCC-TCTGCAAA   2458

Sequenz_1   ****   ---------------- --------------------------------------------   ****
Sequenz_2   2051   GGAAATACCAGTTCTG GGCAATCAGTGTTACCGTTCACCAGTTGCCATTGAGGGTTTCAG   2110
Sequenz_3   2459   GGAAATACCAGTTCTG GGCAATCAGTGTTACCGTTCACCAGTTGCCATTGAGGGTTTCAG   2518

Sequenz_1   ****   ---------------- --------------------------------------------   ****
Sequenz_2   2111   AGAGCCTTTTTCTAGG CCTACATGCTTTGTGAACAAGTCCCTGTAATTGTTGTTTGTATG   2170
Sequenz_3   2519   AGAGCCTTTTTCTAGG CCTACATGCTTTGTGAACAAGTCCCTGTAATTGTTGTTTGTATG   2578

Sequenz_1   ****   ---------------- --------------------------------------------   ****
Sequenz_2   2171   TATAATTCAAAGCACC AAAATAAGAAAAGATGTAGATTTATTTCATCATATTATACAGAC   2230
Sequenz_3   2579   TATAATTCAAAGCACC AAAATAAGAAAAGATGTAGATTTATTTCATCATATTATACAGAC   2638

Sequenz_1   ****   ---------------- --------------------------------------------   ****
Sequenz_2   2231   CGAACTGTTGTATAAA TTTATTTACTGCTAGTCTTAAGAACTGCTTTCTTTCGTTTGTTT   2290
Sequenz_3   2639   CGAACTGTTGTATAAA TTTATTTACTGCTAGTCTTAAGAACTGCTTTCTTTCGTTTGTTT   2698

Sequenz_1   ****   ---------------- --------------------------------------------   ****
Sequenz_2   2291   GTTTCAATATTTTCCT TCTCTCTCAATTTTCGGTTGAATAAACTAGATTACATTCAGTTG   2350
Sequenz_3   2699   GTTTCAATATTTTCCT TCTCTCTCAATTTTCGG---------------------------   2731

Sequenz_1   ****   ---------------- ****
Sequenz_2   2351   GCAAAAAAAAAAAAA                   2365
Sequenz_3   ****   ---------------- ****
```

```
GGCGCCGTCTTGATACTTTCAGAAAGAATGCATTCCCTGTAAAAAAAAAA
AAAAAAAAATACTGAGAGAGGGAGAGAGAGAGAAGAAGAGAGAGAGACGG
AGGGAGAGCGAGACAGAGCGAGCAACGCAATCTGACCGAGCAGGTCGTAC
GCCGCCGCCTCCTCCTCCTCTCTGCTCTTCGCTACCCAGGTGACCCGAGG
AGGGACTCCGCCTCCGAGCGGCTGAGGACCCCGGTGCAGAGGAGCCTGGC
TCGCAGAATTGCAGAGTCGTCGCCCCTTTTTACAACCTGGTCCCGTTTTA
TTCTGCCATACCCAGTTTTTGGATTTTTGTCTTCCCCTTCTTCTCTTTGC
TAAACGACCCCTCCAAGATAATTTTTAAAAAACCTTCTCCTTTGCTCACC
TTTGCTTCCCAGCCTTCCCATCCCCCCACCGAAAGCAAATCATTCAACGA
CCCCCGACCCTCCGACGGCAGGAGCCCCCGACCTCCCAGGCGGACCGCC
CTCCCTCCCCGCGCGGGTTCCGGGCCCGGCGAGAGGGCGCGAGCACAG
CCGAGGCCATGGAGGTGACGGCGGACCAGCCGCGCTGGGTGAGCCACCAC
CACCCCGCCGTGCTCAACGGGCAGCACCCGGACACGCACCACCCGGGCCT
CAGCCACTCCTACATGGACGCGGCGCAGTACCCGCTGCCGGAGGAGGTGG
ATGTGCTTTTTAACATCGACGGTCAAGGCAACCACGTCCCGCCCTACTAC
GGAAACTCGGTCAGGGCCACGGTGCAGAGGTACCCTCCGACCCACCACGG
GAGCCAGGTGTGCCGCCCGCCTCTGCTTCATGGATCCCTACCCTGGCTGG
ACGGCGGCAAAGCCCTGGGCAGCCACCACACCGCCTCCCCCTGGAATCTC
AGCCCCTTCTCCAAGACGTCCATCCACCACGGCTCCCCGGGGCCCCTCTC
CGTCTACCCCCCGGCCTCGTCCTCCTCCTTGTCGGGGGGCCACGCCAGCC
CGCACCTCTTCACCTTCCCGCCCACCCCGCCGAAGGACGTCTCCCCGGAC
CCATCGCTGTCCACCCCAGGCTCGGCCGGCTCGGCCCGGCAGGACGAGAA
AGAGTGCCTCAAGTACCAGGTGCCCCTGCCCGACAGCATGAAGCTGGAGT
CGTCCCACTCCCGTGGCAGCATGACCGCCCTGGGTGGAGCCTCCTCGTCG
ACCCACCACCCCATCACCACCTACCCGCCCTACGTGCCCGAGTACAGCTC
CGGACTCTTCCCCCCCAGCAGCCTGCTGGGCGGCTCCCCCACCGGCTTCG
GATGCAAGTCCAGGCCCAAGGCCCGGTCCAGCACAGAAGGCAGGGAGTGT
GTGAACTGTGGGCAACCTCGACCCCACTGTGGCGGCGAGATGGCACGGG
ACACTACCTGTGCAACGCCTGCGGGCTCT```CACAAA```GAACGGACAGA
ACCGGCCCCTC```TAAGCCCAAGCGAAGGCT```CTGCAGCCAGGAGAGCA
GGGAC```CCT```GCGAACT```CAGACCACCACAACCACACTCTGGAGGAG
GA```GCCA```GGGACCCT```CTGCA```GCCT```GGGCTCTACTACAAGC
TTCACA```TAACAGACCCCTGACT```GAAGAAGGAAGG```CCAGACC
AGAAACCGAAAA```CTAGCAA```CCAAAAA```GCAAAAAA```GC```GA
CTCACTGGAGGACTTCCCCAAGAACAGCTC```TTAACCCGGCCGCCCTCT
CCAGACAC```CCTCCCTGAGCCAC```CTCGCCCTTCAGCCACCCCAGC
CAC```GCTGACCACGCCCACGCCG```GCACCCGCC```CCAGCCT```CCTT
TGGACCACACCACCCCTCCAGC```G```CACCGCC```GG```TAGAGCCCTG
CTCG```GCTCACAGGGCCCCCAGCGAGA```CCCTGCA```CCCTTTCGACT
TGC```TTTTGCAGGAGCA```C```GAAGCCTAAACGCG```GG```
```TTTTGAAGGCAGAAAGCAAA```T```GCTTGCCACTTTGCAAAGGAGCTC
ACT```G```CT```TCCAACCACTGA```CTGGACCCC```CT```GA```A
AGCC```TCTGACTC```CCCCT```TTAACAGG```CTCTA```GCT```GAA
AAAAAAAA```GCTGAACA```TGC```AACTT```T```AAGAA```ACT```
ACA```GACTTT```TGC```CTGG```AGCT```AAGGC```GAAGG```GCCAAG
AA```TTAAGGA```GGGAGAA```AG```GGAA```TAAGAAGAAACTAG```
```CTG```TCAA```GGACAAACTGCCA```TTT```TTCCTTTCACTGGCCA
CA```T```TTGA```GC```TAAAAGAAA```AAAAAAAGAAAAGAGAAAAGA
AAAAAAAAGAAAAAA```T```AGGCGA```C```TT```TCAAAGCT```TGGCC
TCTGCAAAGGAA```ACCA```TCTGGGCA```CA```T```TACC```TCACCA```
TGCC```TGAGG```TTCAGAGAGCCTTTTTCTAGGCCTAC```GCTTT```GA
ACAA```CCCT```A```T```T```TT```T```A```TCAAAGCACCAAA```A
AGAAAG```AGA```TT```TT```C```T```ACAGACCGAACT```T```A
```AAA```TT```TTACTGCTA```CTTAAGAACTGCTTTCTTTC```TT```TT```
TTCA```T```TTTCCTTCTCTCTCA```TTTC
```

| Name | DNAzyme Sequenz |
|---|---|
| td1 | TGGCTTCTAggctagctacaacgaGCCCTCGTC |
| td2 | GGGCTCTGAggctagctacaacgaGCCTGGCTT |
| td3 | GGGACCCCAggctagctacaacgaCGGAGCCCG |
| td4 | GGTGGGGGAggctagctacaacgaCCCACCGGA |
| td5 | GGCGGGGGAggctagctacaacgaCCGAGGGCC |
| td6 | GGGCTGGGAggctagctacaacgaGGGCAGGGA |
| td7 | CGTCGAGGAggctagctacaacgaCCGCCCCTC |
| td8 | GGGCTGGCAggctagctacaacgaCTTCCCGTA |
| td9 | CGATGCCCAggctagctacaacgaCCGGGGCGG |
| td10 | GCTCCACGAggctagctacaacgaGCCCATCCG |
| td11 | CCGGCTCCAggctagctacaacgaGATGCCCAT |
| td12 | TCTCCGCAAggctagctacaacgaCCGGCTCCA |
| td13 | CCGTCAGCAggctagctacaacgaGTCTCCGCA |
| td14 | TCCCCGGCAggctagctacaacgaCGGCTCGGT |
| td15 | CCCCCGCGAggctagctacaacgaGCTCGTCCG |
| td16 | GTAGGGAGAggctagctacaacgaCCCAGGCTG |
| td17 | GGGCGGGCAggctagctacaacgaCAAGGCGCC |
| td18 | CGGGAAGGAggctagctacaacgaTCGCCCGCG |
| td19 | TAGTCCTCAggctagctacaacgaGCGGCCCCG |
| td20 | TCCCCGACAggctagctacaacgaCTCCAGTCC |
| td21 | TTTCCCCGAggctagctacaacgaACCTCCAGT |
| td22 | TGAGCGCGAggctagctacaacgaCCTCAGTTT |
| td23 | GGACCACAAggctagctacaacgaAGGTGGTTG |
| td24 | CTTGGACCAggctagctacaacgaAACAGGTGG |
| td25 | AAACTTGGAggctagctacaacgaCACAACAGG |
| td26 | CTGATTAAAggctagctacaacgaTTGGACCAC |
| td27 | TGGTGCTGAggctagctacaacgaTAAACTTGG |
| td28 | TGATGATCAggctagctacaacgaCTCTGTCTG |
| td29 | TGGTGATGAggctagctacaacgaCATCTCTGT |
| td30 | GCTTGGTGAggctagctacaacgaGATCATCTC |
| td31 | ATGGGAACAggctagctacaacgaCCGCCGTCC |
| td32 | GAATGGGAAggctagctacaacgaATCCGCCGT |
| td33 | TGACAGGAAggctagctacaacgaGGGAACATC |
| td34 | AGTAAATGAggctagctacaacgaAGGAATGGG |
| td35 | CACAGTAAAggctagctacaacgaGACAGGAAT |
| td36 | GCCCGGCCAggctagctacaacgaAGTAAATGA |
| td37 | CCACAAACAggctagctacaacgaCCTGTAGTG |
| td38 | GTCCACAAAggctagctacaacgaATCCTGTAG |
| td39 | CCACGTCCAggctagctacaacgaAAACATCCT |
| td40 | CCAAGACCAggctagctacaacgaGTCCACAAA |
| td41 | CCACCAAGAggctagctacaacgaCACGTCCAC |
| td42 | GCTGGTCCAggctagctacaacgaCAAGACCAC |
| td43 | GCTCTGGTAggctagctacaacgaCGCCAGTGG |
| td44 | CTGCACCCAggctagctacaacgaTTGCCGCTC |
| td45 | CACACTGCAggctagctacaacgaCCACTTGCC |
| td46 | CTTTCCACAggctagctacaacgaTGCACCCAC |
| td47 | GCCTTTCCAggctagctacaacgaACTGCACCC |
| td48 | TTCCTGGCAggctagctacaacgaGCTGCCCTC |

Fig. 7 Cont.

| Name | DNAzyme Sequenz |
|------|-----------------|
| TD49 | GTGGACGTAggctagctacaacgaAGGCGGTTT |
| TD50 | CCGGGTGGAggctagctacaacgaGTACAGGCG |
| TD51 | CCTGGCGCAggctagctacaacgaCCAGTGCGC |
| TD52 | CAAATGAAggctagctacaacgaTTCCTGGCG |
| TD53 | TTTCCCAAAggctagctacaacgaGAAACTTCC |
| TD54 | ATTGTTGGAggctagctacaacgaGCCCCCTTG |
| TD55 | TGGGTCACAggctagctacaacgaTGTTGGACG |
| TD56 | TCTGGGTCAggctagctacaacgaATTGTTGGA |
| TD57 | GCACAATCAggctagctacaacgaCTGGGTCAC |
| TD58 | GGAGCACAAggctagctacaacgaCATCTGGGT |
| TD59 | ACTGGAGCAggctagctacaacgaAATCATCTG |
| TD60 | ATGGAGGGAggctagctacaacgaTGGAGCACA |
| TD61 | TGGTACTTAggctagctacaacgaGGAGGGACT |
| TD62 | GGGCTGGTAggctagctacaacgaTTATGGAGG |
| TD63 | TCAACGATAggctagctacaacgaGCAGCCGGG |
| TD64 | CCTCAACGAggctagctacaacgaATGCAGCCG |
| TD65 | TCACCTCAAggctagctacaacgaGATATGCAG |
| TD66 | CGTCGTTCAggctagctacaacgaCTCAACGAT |
| TD67 | GTAAAGATAggctagctacaacgaGCGTGTTGG |
| TD68 | AAGTAAAGAggctagctacaacgaATGCGTGTT |
| TD69 | GGCAATGAAggctagctacaacgaTGGGTTTCT |
| TD70 | TCACGGCAAggctagctacaacgaGAACTGGGT |
| TD71 | AGGCAGTCAggctagctacaacgaGGCAATGAA |
| TD72 | ATCTCGGCAggctagctacaacgaTCTGGTAGG |
| TD73 | GCTGAGTAAggctagctacaacgaCTCGGCATT |
| TD74 | TATTATCAAggctagctacaacgaTTTCAGCTG |
| TD75 | GGGTTATTAggctagctacaacgaCAATTTTCA |
| TD76 | AAGGGGTTAggctagctacaacgaTATCAATTT |
| TD77 | CTCCCGGAAggctagctacaacgaCCTTTGGCA |
| TD78 | GTACATGGAggctagctacaacgaTCAAAGTTC |

Fig. 8

Multiple Sequenz Alignments T-bet

```
Seq_1    1     CGGCCCGCTGGAGAGGAAGCCCGAGAGCTGCCGCGCGCCTGCCGGACGAGGGCGTAGAAG    60
Seq_2    1     CGGCCCGCTGGAGAGGAAGCCCGAGAGCTGCCGCGCGCCTGCCGGACGAGGGCGTAGAAG    60

Seq_1    61    CCAGGCGTCAGAGCCCGGGCTCCGGTGGGGTCCCCCACCCGGCCCTCGGGTCCCCCGCCC   120
Seq_2    61    CCAGGCGTCAGAGCCCGGGCTCCGGTGGGGTCCCCCACCCGGCCCTCGGGTCCCCCGCCC   120

Seq_1    121   CCTGCTCCCTGCCGATCCCAGCCCACGCGACCCTCTCGCGCGCGGAGGGGCGGGTCCTCG   180
Seq_2    121   CCTGCTCCCTGCCGATCCCAGCCCACGCGACCCTCTCGCGCGCGGAGGGGCGGGTCCTCG   180

Seq_1    181   ACGGCTACGGGAAGGTGCCAGCCCGCCCCGGATGGGCATCGTGGAGCCGGGTTGCGGAGA   240
Seq_2    181   ACGGCTACGGGAAGGTGCCAGCCCGCCCCGGATGGGCATCGTGGAGCCGGGTTGCGGAGA   240

Seq_1    241   CATGCTGACGGGCACCGAGCCGATGCCGGGGAGCGACGAGGGCCGGGCGCCTGGCGCCGA   300
Seq_2    241   CATGCTGACGGGCACCGAGCCGATGCCGGGGAGCGACGAGGGCCGGGCGCCTGGCGCCGA   300

Seq_1    301   CCCCGCAGCAGCGCTACTTCTACCCGGAGCCGGGCGCGCAGGACGCGGACGAGCGTCGCGG   360
Seq_2    301   CCCCGCAGCAGCGCTACTTCTACCCGGAGCCGGGCGCGCAGGACGCGGACGAGCGTCGCGG   360

Seq_1    361   GGGCGGCAGCCTGGGGTCTCCCTACCCGGGGGGCGCCTTGGTGCCCGCCCCGCCGAGCCG   420
Seq_2    361   GGGCGGCAGCCTGGGGTCTCCCTACCCGGGGGGCGCCTTGGTGCCCGCCCCGCCGAGCCG   420

Seq_1    421   CTTCCTTGGAGCCTACGCCTACCCGCCGCGACCCCAGGCGGCCGGCTTCCCCGGCGCGGG   480
Seq_2    421   CTTCCTTGGAGCCTACGCCTACCCGCCGCGACCCCAGGCGGCCGGCTTCCCCGGCGCGGG   480

Seq_1    481   CGAGTCCTTCCCGCCGCCCGCGGACGCCGAGGGCTACCAGCCGGGCGAGGGCTACGCCGC   540
Seq_2    481   CGAGTCCTTCCCGCCGCCCGCGGACGCCGAGGGCTACCAGCCGGGCGAGGGCTACGCCGC   540

Seq_1    541   CCCGGACCCGCGCGCCGGGCTCTACCCGGGGCCGCGTGAGGACTACGCGCTACCCGCGGG   600
Seq_2    541   CCCGGACCCGCGCGCCGGGCTCTACCCGGGGCCGCGTGAGGACTACGCGCTACCCGCGGG   600

Seq_1    601   ACTGGAGGTGTCGGGGAAACTGAGGGTCGCGCTCAACAACCACCTGTTGTGGTCCAAGTT   660
Seq_2    601   ACTGGAGGTGTCGGGGAAACTGAGGGTCGCGCTCAACAACCACCTGTTGTGGTCCAAGTT   660

Seq_1    661   TAATCAGCACCAGACAGAGATGATCATCACCAAGCAGGGACGGCGGATGTTCCCATTCCT   720
Seq_2    661   TAATCAGCACCAGACAGAGATGATCATCACCAAGCAGGGACGGCGGATGTTCCCATTCCT   720

Seq_1    721   GTCATTTACTGTGGCCGGGCTGGAGCCCACCAGCCACTACAGGATGTTTGTGGACGTGGT   780
Seq_2    721   GTCATTTACTGTGGCCGGGCTGGAGCCCACCAGCCACTACAGGATGTTTGTGGACGTGGT   780

Seq_1    781   CTTGGTGGACCAGCACCACTGGCGGTACCAGAGCGGCAAGTGGGTGCAGTGTGGAAAGGC   840
Seq_2    781   CTTGGTGGACCAGCACCACTGGCGGTACCAGAGCGGCAAGTGGGTGCAGTGTGGAAAGGC   840

Seq_1    841   CGAGGGCAGCATGCCAGGAAACCGCCTGTACGTCCACCCGGACTCCCCCAACACAGGAGC   900
Seq_2    841   CGAGGGCAGCATGCCAGGAAACCGCCTGTACGTCCACCCGGACTCCCCCAACACAGGAGC   900
                                                                      td54
Seq_1    901   GCACTGGATGCGCCAGGAAGTTTCATTTGGGAAACTAAAGCTCACAAACAA           960
Seq_2    901   GCACTGGATGCGCCAGGAAGTTTCATTTGGGAAACTAAAGCTCACAAACAACAAGGGGGC   960

Seq_1    961            GTGACCCAGATGATTGTGCTCCAGTCCCTCCATAAGTACCAGCCCCGGCT  1020
Seq_2    961   GTCCAACAATGTGACCCAGATGATTGTGCTCCAGTCCCTCCATAAGTACCAGCCCCGGCT  1020

Seq_1    1021  GCATATCGTTGAGGTGAACGACGGAGAGCCAGAGGCAGCCTGCAACGCTTCCAACACGCA  1080
Seq_2    1021  GCATATCGTTGAGGTGAACGACGGAGAGCCAGAGGCAGCCTGCAACGCTTCCAACACGCA  1080
                                       td69              td70
Seq_1    1081  TATCTTTACTTTCCA                           GTGACTGCCTACCAGAATGCCGAGAT  1140
Seq_2    1081  TATCTTTACTTTCCAAGAAACCCAGTTCATTGCCGTGACTGCCTACCAGAATGCCGAGAT  1140

Seq_1    1141  TACTCAGCTGAAAATTGATAATAACCCCTTTGCCAAAGGATTCCGGGAGAACTTTGAGTC  1200
Seq_2    1141  TACTCAGCTGAAAATTGATAATAACCCCTTTGCCAAAGGATTCCGGGAGAACTTTGAGTC  1200

Seq_1    1201  CATGTACACATCTGTTGACACCAGCATCCCCTCCCCGCCTGGACCCAACTGTCAATTCCT  1260
Seq_2    1201  CATGTACACATCTGTTGACACCAGCATCCCCTCCCCGCCTGGACCCAACTGTCAATTCCT  1260

Seq_1    1261  TGGGGGAGATCACTACTCTCCTCTCCTACCCAACCAGTATCCTGTTCCCAGCCGCTTCTA  1320
Seq_2    1261  TGGGGGAGATCACTACTCTCCTCTCCTACCCAACCAGTATCCTGTTCCCAGCCGCTTCTA  1320

Seq_1    1321  CCCCGACCTTCCTGGCCAGGCGAAGGATGTGGTTCCCAGGCTTACTGGCTGGGGGCCCC   1380
Seq_2    1321  CCCCGACCTTCCTGGCCAGGCGAAGGATGTGGTTCCCAGGCTTACTGGCTGGGGGCCCC   1380

Seq_1    1381  CCGGGACCACAGCTATCGGCTGAGTTTCGAGCAGTCAGCATGAAGCCTGCATTCTTGCC  1440
Seq_2    1381  CCGGGACCACAGCTATCGGCTGAGTTTCGAGCAGTCAGCATGAAGCCTGCATTCTTGCC  1440
```

Fig. 8 Cont.

```
Seq_1   1441  CTCTGCCCCTGGGCCCACCATGTCCTACTACCGAGGCCAGGAGGTCCTGGCACCTGGAGC  1500
Seq_2   1441  CTCTGCCCCTGGGCCCACCATGTCCTACTACCGAGGCCAGGAGGTCCTGGCACCTGGAGC  1500

Seq_1   1501  TGGCTGGCCTGTGGCACCCCAGTACCCTCCCAAGATGGGCCCGGCCAGCTGGTTCGGCCC  1560
Seq_2   1501  TGGCTGGCCTGTGGCACCCCAGTACCCTCCCAAGATGGGCCCGGCCAGCTGGTTCAGCCC  1560

Seq_1   1561  TATGCGGACTCTGCCCATGGAACCCGGCCCTGGAGGCTCAGAGGGACGGGGACCAGAGGA  1620
Seq_2   1561  TATGCGGACTCTGCCCATGGAACCCGGCCCTGGAGGCTCAGAGGGACGGGGACCAGAGGA  1620

Seq_1   1621  CCAGGGTCCCCCCTTGGTGTGGACTGAGATTGCCCCCATCCGGCCGGAATCCAGTGATTC  1680
Seq_2   1621  CCAGGGTCCCCCCTTGGTGTGGACTGAGATTGCCCCCATCCGGCCGGAATCCAGTGATTC  1680

Seq_1   1681  AGGACTGGGCGAAGGAGACTCTAAGAGGAGGCGCGTGTCCCCCTATCCTTCCAGTGGTGA  1740
Seq_2   1681  AGGACTGGGCGAAGGAGACTCTAAGAGGAGGCGCGTGTCCCCCTATCCTTCCAGTGGTGA  1740

Seq_1   1741  CAGCTCCTCCCCTGCTGGGGCCCCTTCTCCTTTTGATAAGGAAGCTGAAGGACAGTTTTA  1800
Seq_2   1741  CAGCTCCTCCCCTGCTGGGGCCCCTTCTCCTTTTGATAAGGAAGCTGAAGGACAGTTTTA  1800

Seq_1   1801  TAACTATTTTCCCAACTGAGCAGATGACATGATGAAAGGAACAGAAACAGTGTTATTAGG  1860
Seq_2   1801  TAACTATTTTCCCAACTGAGCAGATGACATGATGAAAGGAACAGAAACAGTGTTATTAGG  1860

Seq_1   1861  TTGGAGGACACCGACTAATTTGGGAAACGGATGAAGGACTGAGAAGGCCCCCGCTCCCTC  1920
Seq_2   1861  TTGGAGGACACCGACTAATTTGGGAAACGGATGAAGGACTGAGAAGGCCCCCGCTCCCTC  1920

Seq_1   1921  TGGCCCTTCTCTGTTTAGTAGTTGGTTGGGGAAGTGGGGCTCAAGAAGGATTTTGGGGTT  1980
Seq_2   1921  TGGCCCTTCTCTGTTTAGTAGTTGGTTGGGGAAGTGGGGCTCAAGAAGGATTTTGGGGTT  1980

Seq_1   1981  CACCAGATGCTTCCTGGCCCACGATGAAACCTGAGAGGGGTGTCCCCTTGCCCCATCCTC  2040
Seq_2   1981  CACCAGATGCTTCCTGGCCCACGATGAAACCTGAGAGGGGTGTCCCCTTGCCCCATCCTC  2040

Seq_1   2041  TGCCCTAACTACAGTCGTTTACCTGGTGCTGCGTCTTGCTTTTGGTTTCCAGCTGGAGAA  2100
Seq_2   2041  TGCCCTAACTACAGTCGTTTACCTGGTGCTGCGTCTTGCTTTTGGTTTCCAGCTGGAGAA  2100

Seq_1   2101  AAGAAGACAAGAAAGTCTTGGGCATGAAGGAGCTTTTTGCATCTAGTGGGTGGGAGGGGT  2160
Seq_2   2101  AAGAAGACAAGAAAGTCTTGGGCATGAAGGAGCTTTTTGCATCTAGTGGGTGGGAGGGGT  2160

Seq_1   2161  CAGGTGTGGGACATGGGAGCAGGAGACTCCACTTTCTTCCTTTGTACAGTAACTTTCAAC  2220
Seq_2   2161  CAGGTGTGGGACATGGGAGCAGGAGACTCCACTTTCTTCCTTTGTACAGTAACTTTCAAC  2220

Seq_1   2221  CTTTTCGTTGGCATGTGTGTTAATCCCTGATCCAAAAAGAACAAATACACGTATGTTATA  2280
Seq_2   2221  CTTTTCGTTGGCATGTGTGTTAATCCCTGATCCAAAAAGAACAAATACACGTATGTTATA  2280

Seq_1   2281  ACCATCAGCCCGCCAGGGTCAGGGAAAGGACTCACCTGACTTTGGACAGCTGGCCTGGGC  2340
Seq_2   2281  ACCATCAGCCCGCCAGGGTCAGGGAAAGGACTCACCTGACTTTGGACAGCTGGCCTGGGC  2340

Seq_1   2341  TCCCCCTGCTCAAACACAGTGGGGATCAGAGAAAAGGGGCTGGAAAGGGGGGAATGGCCC  2400
Seq_2   2341  TCCCCCTGCTCAAACACAGTGGGGATCAGAGAAAAGGGGCTGGAAAGGGGGGAATGGCCC  2400

Seq_1   2401  ACATCTCAAGAAGCAAGATATTGTTTGTGGTGGTTGTGTGTGGGTGTGTGTTTTTCTTT   2460
Seq_2   2401  ACATCTCAAGAAGCAAGATATTGTTTGTGGTGGTTGTGTGTGGGTGTGTG----------  2450

Seq_1   2461  TTCTTTCTTTTTATTTTTTTTGAATGGGGGAGGCTATTTATTGTACTGAGAGTGGTGTCT  2520
Seq_2   **  ------------------------------------------------------------  **

Seq_1   2521  GGATATATTCCTTTTGTCTTCATCACTTTCTGAAAATAAACATAAAACTGTTAAAAAAAA  2580
Seq_2   **  ------------------------------------------------------------  **

Seq_1   2581  AAAAAAAA                                                     2589
Seq_2   **  ---------                                                    **
```

```
CGGCCCGCTGGAGAGGAAGCCCGAGAGCTGCCGCGCGCCTGCCGGACGAG
GGCGTAGAAGCCAGGCGTCAGAGCCCGGGCTCCGGTGGGGTCCCCCACCC
GGCCCTCGGGTCCCCCGCCCCTGCTCCCTGCCCATCCCAGCCCACGCGA
CCCTCTCGCGCGCGGAGGGGCGGGTCCTCGACGGCTACGGGAAGGTGCCA
GCCCGCCCCGGATGGGCATCGTGGAGCCGGGTTGCGGAGACATGCTGACG
GGCACCGAGCCGATGCCGGGGAGCGACGAGGGCCGGGCGCCTGGCGCCGA
CCCGCAGCACCGCTACTTCTACCCGGAGCCGGGCGCGCAGGACGCGGACG
AGCGTCGCGGGGCGGCAGCCTGGGGTCTCCCTACCCGGGGGGCGCCTTG
GTGCCCGCCCCGCCGAGCCGCTTCCTTGGAGCCTACGCCTACCCGCCGCG
ACCCCAGGCGGCCGGCTTCCCCGGCGCGGGCGAGTCCTTCCCGCCGCCCG
CGGACGCCGAGGGCTACCAGCCGGGCGAGGGCTACGCCGCCCCGGACCCG
CGCGCCGGGCTCTACCCGGGGCCGCGTGAGGACTACGCGCTACCCGCGGG
ACTGGAGGTGTCGGGGAAACTGAGGGTCGCGCTCAACAACCACCTGTTGT
GGTCCAAGTTTAATCAGCACCAGACAGAGATGATCATCACCAAGCAGGGA
CGGCGGATGTTCCCATTCCTGTCATTTACTGTGGCCGGGCTGGAGCCCAC
CAGCCACTACAGGATGTTTGTGGACGTGGTCTTGGTGGACCAGCACCACT
GGCGGTACCAGAGCGGCAAGTGGGTGCAGTGTGGAAAGGCCGAGGGCAGC
ATGCCAGGAAACCGCCTGTACGTCCACCCGGACTCCCCCAACACAGGAGC
GCACTGGATGCGCCAGGAAGTTTCATTTGGGAAACTAAAGCTCACAAACA
ACAAGGGGGCGTCCAACAATGTGACCCAGATGATTGTGCTCCAGTCCCTC
CATAAGTACCAGCCCCGGCTGCATATCGTTGAGGTGAACGACGGAGAGCC
AGAGGCAGCCTGCAACGCTTCCAACACGCATATCTTTACTTTCCAAGAAA
CCCAGTTCATTGCCGTGACTGCCTACCAGAATGCCGAGATTACTCAGCTG
AAAATTGATAATAACCCCTTTGCCAAAGGATTCCGGGAGAACTTTGAGTC
C……ACAC……CT……TGACACCAGC……CCCCTCCCCGCCTGGACCCAACT
……CA……TCCTTGGGGAG……CACTACTCCTCTCCTACCCAACCA……
CCT……TCCCAGCCGCTTCTACCCCGACCTTCCTGGCCAGGCGAAG……
G……TCCCCAGGCTTACTGGCTGGGGGCCCCCGGGACCACAGCT……GAGG
CTGA……TTCGAGCA……CAGC……GAAGCCTGC……TCTTGCCCTCTGCCCCT
GGGCCCACC……CCTACTACCGAGGCCAGGAGG……CCTGGCACCTGGAGC
TGGCTGGCCT……GGCACCCCA……ACCCTCCCAAG……GGGCCCGGCCAGCT
G……TCCGCCCT……GCGGACTCTGCCC……GGAACCCGGCCCTGGAGGCTCA
GAGGGACGGGGACCAGAGGACCAGG……CCCCCCTTG……GGACTGAG……
TGCCCCC……CCGGCCGGA……CCA……G……TCAGGACTGGGCGAAGGAGACT
CTAAGAGGAGGCGC……CCCCTA……CCTTCCA……G……GACAGCTCCTCC
CCTGCTGGGGCCCCTTCTCCTTTTG……AAGGAAGCTGAAGGACA……TTT……
……AACT……TTTCCCAACTGAGCAGA……GAC……G……GAAAGGAACAGAAACA……
……TA……TAG……TGGAGGACACCGACTA……TTGGGAAACGG……GAAGGACT
GAGAAGGCCCCCGCTCCCTCTGGCCCTTCTCT……TTA……A……TG……TGGG
GAA……GGGGCTCAAGAAGG……TTTGGG……TCACCAG……GCTTCCTGGCCC
ACG……GAAACCTGAGAGGG……………CCCCTTGCCCC……CCTCTGCCCTAACT
ACA……C……TTACCTG……GCTGC……CTTGCTTTTG……TTCCAGCTGGAGAA
AAGAAGACAAGAAA……CTTGGGCA……GAAGGAGCTTTTTGC……CTA……GC……
……GGGAGGG……CAG……………GGGAC……GGGAGCAGGAGACTCCACTTTCTTCC
TTT……ACA……AACTTTCAACCTTTT……TGGCA……………TA……CCCTG……
……CCAAAAGAACAAA……ACAC………………TA……AACC……CAGCCCGCCAGG……C
AGGGAAAGGACTCACCTGACTTTGGACAGCTGGCCTGGGCTCCCCCTGCT
CAAACACA……GGGGA……CAGAGAAAAGGGGCTGGAAAGGGGGGA……GGCCC
AC……TCAAGAAGCAAG……T……TT……GG……G……T………………GG……G……
……TTTTTCTTTTCTTTCTTTT……TTTTTTTGAATGGGGGAGGCT……TT…
…T……ACTGAGA……G……G……CTGG……………TCCTTTT……CTTC……CACTTTC
TGAAA……AAAC……AAAACT……TAAAAAAAAAAAAAAAAA
```

Fig. 8A

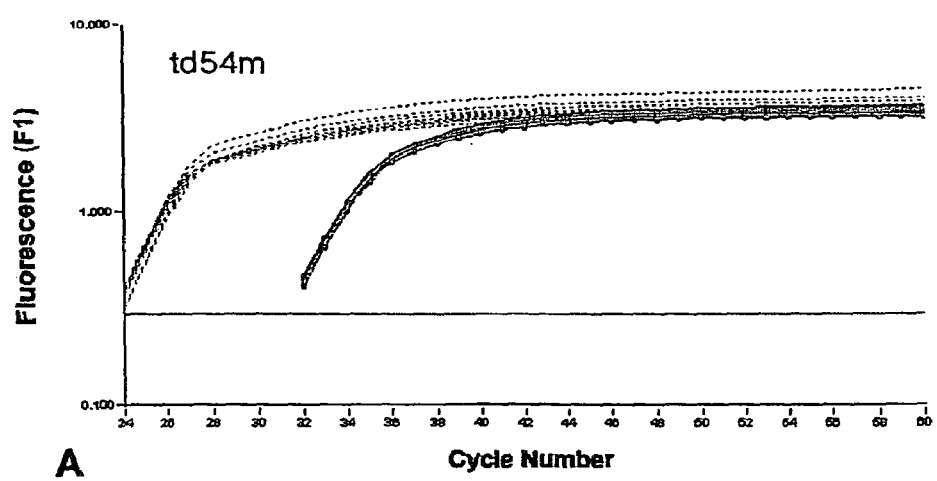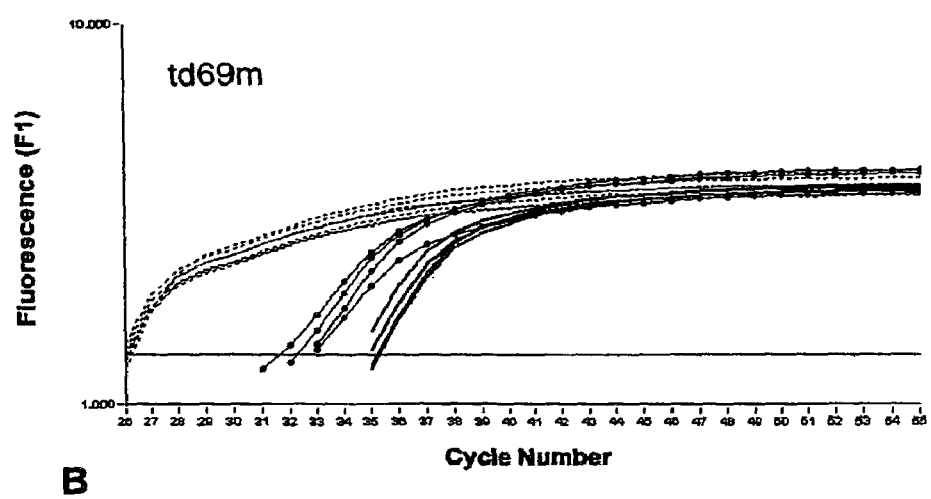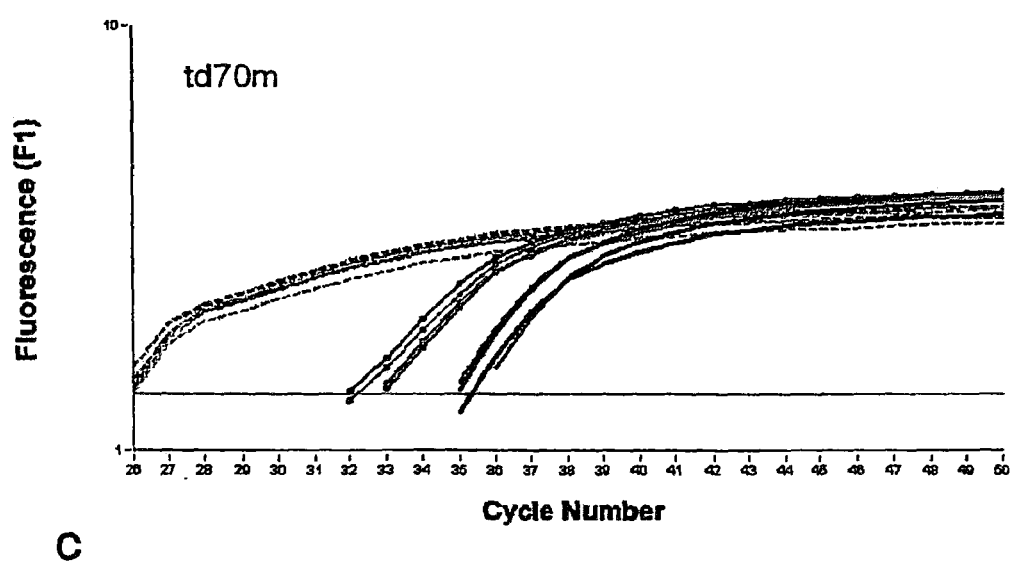
Fig. 10

METHOD FOR THE PRODUCTION OF A CELL AND/OR TISSUE AND/OR DISEASE PHASE SPECIFIC MEDICAMENT

The present invention relates to a method for producing of a cell and/or tissue and/or disease phase specific medicament suitable for the treatment of chronic inflammatory diseases.

BACKGROUND OF THE INVENTION

Chronic inflammatory diseases constitute an increasing medical problem area with a high socio-economic impact. These include in particular the following disease groups:
- Autoimmune diseases and rheumatic diseases (manifestations on skin, lungs, kidney, vascular system, connective tissue, musculoskeletal system, endocrine system, among other)
- Immediate-type allergic reactions and asthma
- Chronic obstructive pulmonary diseases (COPD)
- Arteriosclerosis
- Psoriasis and contact eczema
- Chronic rejection reactions after organ or bone marrow transplant In the last decades, many of these diseases are showing a rising prevalence, not only in the industrial nations, but partly, worldwide. Thus, in Europe, North America, Japan and Australia, more than 20% of the population already suffers from allergic diseases and asthma. Chronic obstructive pulmonary diseases are currently the fifth most common cause of death worldwide and, according to calculations by WHO, will become the third most common cause of death by the year 2020. Arteriosclerosis, with the secondary diseases myocardial infarction, stroke and peripheral arterial occlusion disease, occupy a leading position in the global morbidity and mortality statistics. Psoriasis and contact eczema are, together with neurodermatitis, the most common chronic inflammatory skin diseases.

The so far only insufficiently understood interactions between environmental factors and genetic disposition result in a subsequent defective regulation of the immune system. Here, the following common principles can be established for these different diseases:

(A) An excessive immune response against antigens, which would normally be harmless for humans, is found. These antigens can be environmental matter (e.g. allergens such as pollen, animal hairs, food, mites, chemical substances such as preservatives, dyes, cleaning products). In these cases, the patients develop an allergic reaction. In the case of, for example, active and passive cigarette smoking, chronic obstructive pulmonary diseases (COPD) occur. On the other hand, the immune system can, however, also react against the components of the own organism, recognize them as foreign and start an inflammatory reaction against them. An autoimmune disease develops in these cases. In all cases, harmless, non-toxic antigens are recognized as foreign or dangerous and an inappropriate inflammatory reaction is started.

(B) The diseases proceed in phases which include initiation, progression, i.e. progressing of the inflammatory reaction, and the associated destruction and alteration with loss in organ functionality (so-called remodelling).

(C) The diseases present patient specific subphenotypic characteristic features.

(D) Components of the innate and acquired immunity are later involved in the initiation, maintenance and in the destruction and alteration processes. Under the influence of the innate immunity (important components: antigen presenting cells with their diverse populations and the complement system), the cells of the adaptive immune system (important components: T- and B-lymphocytes) are activated and differentiated. T-cells take over central functions in the following process by differentiating into highly specialized effectors. In doing so, they activate and acquire certain effector mechanisms, including, in particular, the following functions: Production of antibodies, control of the functionality of effector cells of the immune system (such as, for example, neutrophil, basophil, eosinophil granulocytes), feeding back on functions of the innate immune system, influencing the functionality of non-hematopoietic cells, e.g. epithelium, endothelium, connective tissue, bone and cartilage, and, in particular, neuronal cells. This amounts to a special interaction between immune and nervous system, which has led to the development of the concept of neuro-immunological interaction in chronic inflammations.

Due to the complexity and variety of the disease patterns associated with chronic inflammations, an optimal medicament for the treatment of the diseases must meet the following requirements:

(1) Diseases manifest themselves in patient specific (sub) phenotypes. Medicaments must therefore possess a high patient or case specificity.

(2) Diseases proceed in stages and phases. Medicaments must therefore possess a high stage or phase specificity.

(3) The diseases are regulated by cells of different specialization. Medicaments must therefore cause a cell specific intervention.

(4) The diseases manifest themselves in different organs and compartments. Medicaments must therefore possess a high compartment or organ specificity.

(5) Medicaments must be suitable for a long-term therapy. Immune system reactions against the medicaments must therefore be prevented.

(6) The side effect profile of the medicaments must present an acceptable medical and ethical balance between severity index, prognosis and progress of the disease.

None of the currently available established therapies against chronic inflammations meets these criteria in an optimal way. The treatment with immunoglobulin A is known from DE 695 11 245 T2, and the inhibition of phospholipase $A_2$ ($PLA_2$) and/or coenzyme A-independent transacylase (CoA-IT) is known from DE 695 18 667 T2. For this disease, the currently established therapy concepts are centred on unspecific anti-inflammatory therapy, as well as immune suppression. Many of the applied unspecific anti-inflammatory substances, such as ibuprofen, acetylsalicylic acid and paracetamol, are either not effective enough or are afflicted with a high rate of unwanted side effects. Steroids may have, in contrast, a higher potency, but are themselves afflicted with serious side effects, such as hypertonia, diabetes and osteoporosis. New generation immune suppressing medicaments, such as, for example, cyclosporine and tacrolimus, present hepato- and nephrotoxicity.

This situation has led to the search for and the clinical testing of a plurality of new molecules intended to act more specifically on immunological and cell biological defective regulation. These include cytokines, cytokine receptors and anti-cytokines. Problems related to these new therapeutic applications include a lack of cell and organ specificity, development of unwanted immune reactions against these molecules, and poor effectiveness for different phenotypes.

In recent years, attempts are being made to use a new class of catalytic molecules, the so-called "DNAzymes" (Santoro 1997), as therapeutic agents for inactivating genes, the expression of which is the cause of diseases. DNAzymes are single stranded molecules which can, in principle, bind to complementary areas of the RNA and inactivate it through cleavage. The specific use of DNAzymes as therapeutic agents requires, however, that the genes causing the disease, as well as their RNA, are known in detail. This is so far only the case for few diseases.

The DNAzyme described in WO 01/11023A1 binds RelA (p65) mRNA and is thus directed against the transcription factor NF-κB; WO 00/42173 discloses an EGR-1 mRNA binding DNAzyme. WO99/50452 discloses a 10-23 DNAzyme that can be used in a diagnostic method for detecting nucleic acid mutations. None of the currently known antisense molecules and DNAzymes can be used for producing a medicament for the treatment of chronic inflammations in patients.

OBJECT OF THE INVENTION

The object of the present invention is the provision of cell and/or tissue and/or disease phase specific medicaments which lead to the functional inactivation of ribonucleic acid molecules of transcription factors and factors of signal transduction pathways, the expression of which is involved in the development of chronic inflammatory reactions and autoimmune diseases, and which are suitable for the treatment of chronic inflammatory reactions and autoimmune diseases, thus eliminating the abovementioned disadvantages of the state of the art.

It is a further object of the invention to provide a method for producing cell and/or tissue and/or disease phase specific medicaments, which identifies ribonucleic acid molecules of transcription factors and factors of signal transduction pathways, the expression of which is involved in the development of chronic inflammatory reactions and autoimmune diseases, and functionally inactivates them in target cells.

According to the present invention this object is solved by a method using specific DNAzymes according to the present invention as defined herein after.

The invention relates to a DNAzyme which binds to GATA-3 mRNA and functionally inactivates it, which comprises:
  a catalytic domain with the nucleotide sequence GGCTAGCTACAACGA SEQ ID NO: 154 or a modified sequence with comparable biological effect, which cleaves the GATA-3 mRNA at every purine:pyrimidine binding site to which it is bonded,
  a right substrate binding domain adjoining the 3' end of the catalytic domain having polynucleotide sequence GTCTTGGAG and
  a left substrate binding domain adjoining the 5' end of the catalytic domain having polynucleotide sequence GTGGATGGA, both substrate binding domains being respectively complementary to two regions of the GATA 3 mRNA so that they hybridize with the mRNA, and which is active in vivo.

In a preferred feature of the invention, the DNAzyme comprises sequence hgd 40 GTGGATGGA GGCTAGCTACAACGA GTCTTGGAG which is SEQ ID NO: 40.

In particular the invention relates to a DNAzyme which cleaves the catalytic domain of the GATA-3 mRNA at every purine:uracil binding site.

Furthermore the DNAzyme according to the present invention is stabilized against decomposition within the organism by introduction of a 3'-3' inversion.

Another preferred feature of the invention relates to a DNAzyme which is stabilized against decomposition within the organism by introduction of modified nucleotides or nucleotide compounds.

A particular feature of the invention relates to a DNAzyme which includes an inverse thymidine on the 3' end and/or a FAM label on the 5' end.

The invention also relates to A medicament containing a DNAzyme according to the present invention and a pharmaceutically acceptable carrier.

The advantage of the invention lies in a functional inactivation of ribonucleic acid molecules of transcription factors and factors of signal transduction pathways for differentiation and/or expression of cytokines which are involved in the development of chronic inflammatory reactions and autoimmune diseases, by means of specific DNAzymes and/or siRNA. This strategy distinguishes itself from conventional but also gene therapeutic approaches by a very high cell and/or tissue and/or disease phase specificity and selectivity, high stability of the molecules and negligible antigenicity. Optimal preconditions for a tailored long-term therapy for patients with chronic inflammatory diseases are created.

Further details and advantages of the present invention will become apparent from the following figure and description. The following is shown:

BRIEF DESCRIPTION OF THE DRAWINGS

FIG. 3: Pool of specific ribonucleic acid molecules according to step b) particularly the DNAzymes hgd 1 to hgd 70 against GATA-3 and their nucleotide sequences (A=Adenine, G=Guanine, C=Cytosine, T=Thymine). Nucleotides written in uppercase mark a right and left substrate binding domain, nucleotides written in lowercase mark the central catalytic domain of the 10-23 DNAzyme.

FIG. 4: Nucleotide sequences of human GATA-3 genes in alignment.

Sequence 1: Human GATA-3 from database no.: XM_043124.

Sequence 2: Human GATA-3 from database no.: X58072.

Sequence 3: Human GATA-3 (sequenced from plasmid pCR2.1).

Divergent bases are highlighted in grey, primer locations for GATA-3 cloning are underlined. The localisation of the DNAzyme hgd40 is pointed out with bold letters which are also highlighted in grey and underlined.

(A=Adenine, G=Guanine, C=Cytosine, T=Thymine)

FIG. 4 A: Nucleotide sequence 3 of human GATA-3 gene from FIG. 4, into which the individual nucleotide pairs GT and AT have been drawn (highlighted in grey), between which there are further DNAzyme cleavage sites.

Figure 5:
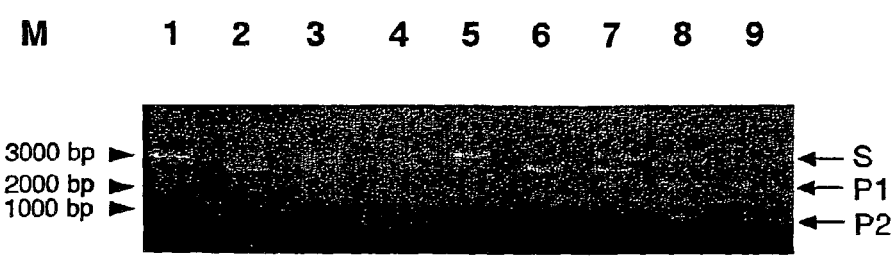

FIG. 5: Gel electrophoresis showing the cleavage of a target mRNA (here GATA-3 mRNA) with specific ribonucleic acid molecules according to step b), here unmodified DNAzymes [hgd11 (lane 2), hgd13 (lane 4), hgd17 (lane 6), hgd40 (lane 8)] and modified DNAzymes [hgd11-M (lane 3), hgd13-M (lane 5), hgd17-M (lane 7), hgd40-M (lane 9)]. M designates the modified DNAzymes. Unmodified (0.25 µM) or modified DNAzymes (0.25 µM) are incubated for one hour at 37° C. with in vitro transcribed GATA-3 mRNA (0.025 µM) in a volume of 10 µl comprising the following reaction composition: 50 mM Tris pH 7.4, 150 mM NaCl, 10 mM $MgCl_2$. The products are subsequently separated by means of gel electrophoresis. Lane 1 contains a control mRNA with no added DNAzyme. A length standard run in parallel (not shown) shows band sizes of 1000 bp, 2000 by and 3000 bp. The arrows point at S, the band containing the substrate (here GATA-3 mRNA) and the cleavage products P1 and P2.

Figure 6:
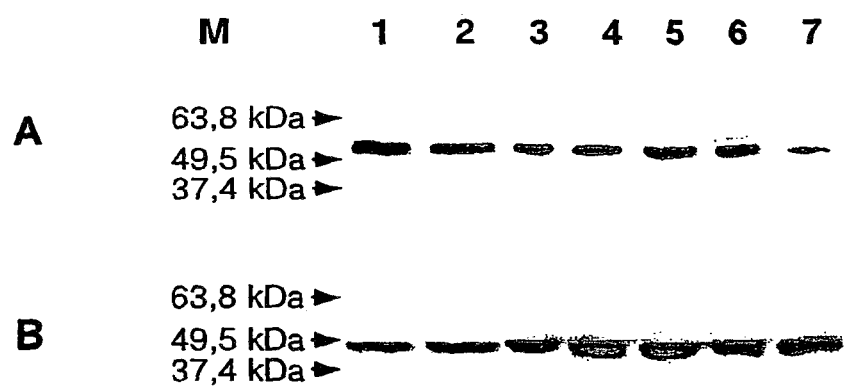

FIG. 6: Immunoblot with the reaction of specific ribonucleic acid molecules in cells. Jurkat E6.1 cells are transfected by means of lipofection with specific ribonucleic acid molecules, here DNAzymes [hgd11-M (lane 4), hgd13-M (lane 5), hgd17-M (lane 6), hgd40-M (lane 7)]. Untreated cells (lane 1), cells only treaded with transfection medium (lane 2), and cells treated with DNAzymes (hgd11-M) with no transfection medium (lane 3) were used for control purposes. After 48 h of incubation, the solubilized proteins are separated by means of SDS-PAGE and GATA-3 (A) detected by immunoblot with specific antibodies. (Lane 4 contains cells with hgd11-M, lane 5 contains cells with hgd13-M, lane 6 contains cells with hgd17-M, lane 7 contains cells with hgd40-M.) To verify that the same protein quantities are present in each lane, immunostaining with β-actin (B) is carried out on the same blot membrane. The length standard run in parallel (not shown) shows band sizes of 63.8 kDa, 49.5 kDa and 37.4 kDa.

FIG. 7: Pool of specific ribonucleic acid molecules according to step b) particularly the DNAzymes td 1 to td 70 against T-bet and their nucleotide sequences (A=Adenine, G=Guanine, C=Cytosine, T=Thymine).

FIG. 8: Nucleotide sequences of human T-bet genes in alignment.

Sequence 1: Human T-bet from database no.: NM_013351.

Sequence 2: Human T-bet (sequenced from pBluescript-SK).

Divergent bases are highlighted in grey, primer locations for T-bet cloning are underlined. The primer locations for the relative quantification on the LightCycler are circled. The localisation of the DNAzymes td54 and td69 is highlighted in grey and underlined at the same time, td70 is additionally highlighted in bold letters.

(A=Adenine, G=Guanine, C=Cytosine, T=Thymine)

FIG. 8A: Nucleotide sequence 1 of human T-bet gene from FIG. 8, the individual nucleotide pairs GT and AT drawn therein, highlighted in grey, between which there are further DNAzyme cleavage sites.

Figure 9:
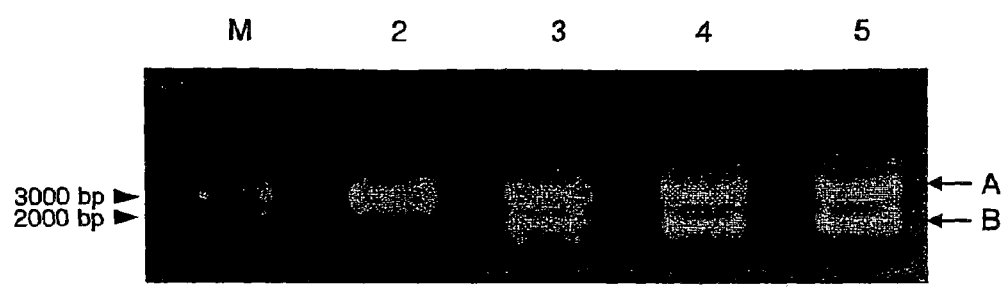

FIG. 9: Gel electrophoresis showing the cleavage of a target mRNA (here T-bet mRNA) with specific ribonucleic acid molecules according to step b), here modified DNAzymes [td54m (lane 3), td69m (lane 4) and td70m (lane 5)]. The modified DNAzymes (0.25 µM) are incubated for 30 min at 37° C. with in vitro transcribed T-bet mRNA (0.025 µM) in a volume of 10 µl comprising the following reaction composition: 50 mM Tris pH 7.4, 150 mM NaCl, 10 mM $MgCl_2$. The products are subsequently separated by means of gel electrophoresis. Lane M contains a 3000 base and 2000 base length standard run in parallel, lane 2 contains a control mRNA with no added DNAzyme. Arrow A points at the band with substrate (here T-bet mRNA), arrow B points at the larger cleavage product. The second cleavage product is smaller and no longer visible in this figure.

FIG. 10: Quantification on the LightCycler of T-bet and GAPDH mRNA from cells treated with DNAzymes td54 (A), td69 (B) and td70 (C). Jurkat E6.1 cells are transfected twice in a period of 24 h, either with the T-bet specific DNAzymes td54 (A), td69 (B) and td70 (C) or with nonsense DNAzymes for control (not shown). After subsequent cleaning with RNA, a reverse transcription is carried out and the obtained DNA introduced in the LightCycler. GAPDH (dashed lines) is used as internal standard. Shown are 4 measurements each of cells treated with T-bet specific DNAzymes or nonsense DNAzyme. The solid lines show the quantity of T-bet in the cells treated with T-bet specific DNAzymes, dotted lines show the quantity of T-bet in the cells treated with nonsense DNAzyme.

Figure 11:
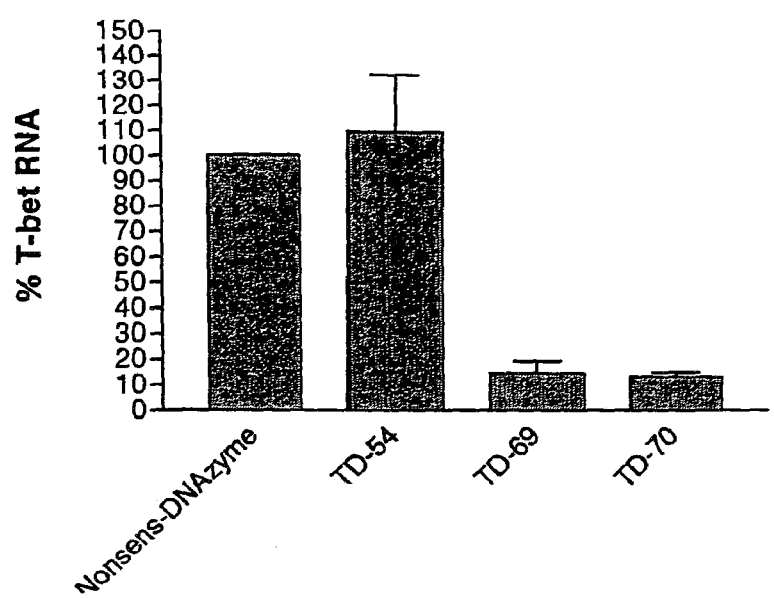

FIG. 11: Diagram of the relative quantification of T-bet mRNA in Jurkat E6.1 cells.

Jurkat E6.1 cells are transfected twice with T-bet specific DNAzymes td54, td69 and td70, and isolated with RNA after 48 h. After a reverse transcription, the quantity of mRNA is determined by means of LightCycler. Nonsense DNAzyme is used as control. The relative quantification of T-bet and GAPDH mRNA is carried out according to instructions [described in the User Bulletin #2 (ABI Prism 7700 Sequence detection System User Bulletin #2 (2001). Relative quantification of gene expression.

Http://docs.appliedbiosystems.com/pebiodocs/04303859.pdf)]. Here, the quantity of T-bet mRNA from the control test with nonsense DNAzyme is set equal to 100%.

Figure 1:
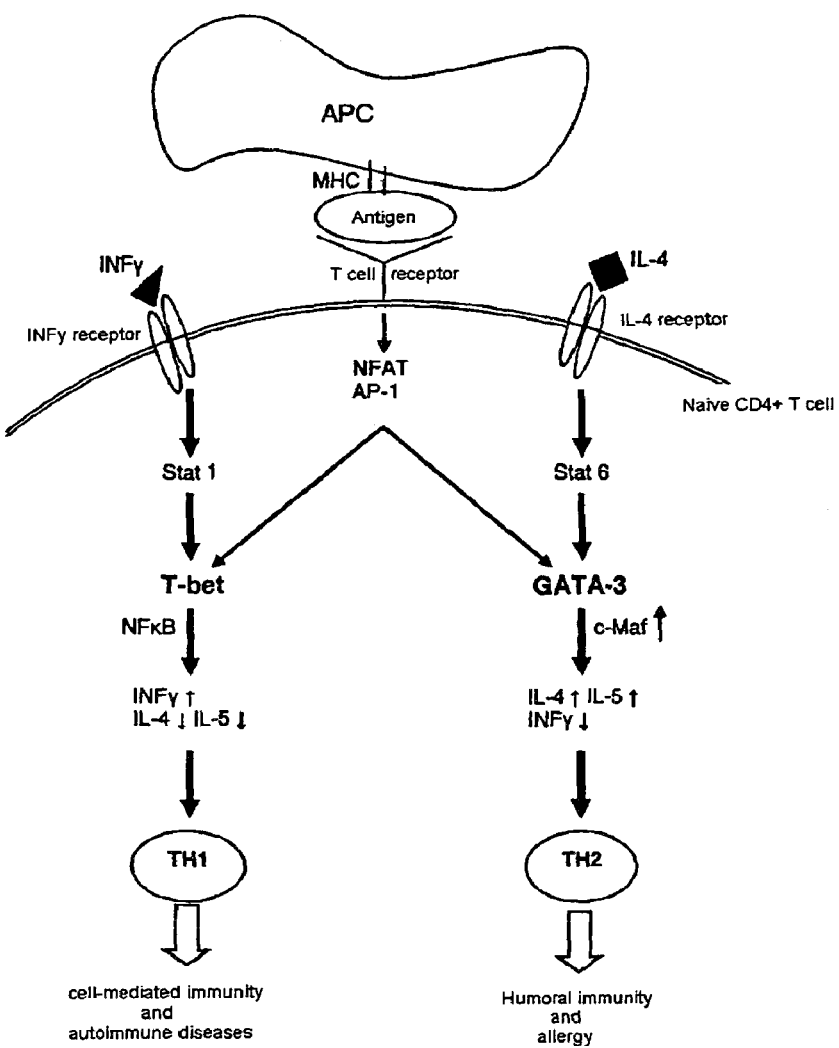
FIG. 1: schematic representation of the signal transduction during differentiation of CD4+ cells to TH1 and TH2 cells, respectively (modified according to Ho I. C. and Glimcher L. H., Cell 2002; 109; S109-S120).

FIG. 1 shows a schematic representation, modified according to Ho I. C. and Glimcher L. H., Cell 2002; 109; S109-S120, of the dynamics of the signal transduction during differentiation of $CD4^+$ cells to TH1 and TH2 cells, respectively. Stimulation via the T cell receptor through the respective peptide-MHC complex induces the clonal expansion and programmed differentiation of $CD4^+$ T lymphocytes to T helper (TH)1 or TH2 cells. Discrimination between these two subtypes takes place on the basis of their cytokine profiles. TH1 cells produce interferon-y (INFy), interleukin 2 (IL-2) and tumour necrosis factor-β, whereas TH2 cells secrete IL-4, IL-5, IL-9 and IL-13. Bacterial and viral infections induce an immune response that is dominated by TH1 cells. On the other hand, TH2 cells regulate the production of IgE against parasites. TH1 and TH2 cells are in equilibrium with each other. The destruction of this equilibrium causes diseases, an excessive TH1 cell response being associated with autoimmune diseases, while an increased TH2 cell response is the origin of allergic diseases.

It is known that TH1 cytokines are involved in the pathogenesis of autoimmune diseases such as, for example, autoimmune uveitis, experimental allergic encephalomyelitis, type 1 diabetes mellitus or Crohn's disease, while TH2 cytokines (IL-4, IL-5, IL-13 or IL-9) take part in the development of chronic inflammatory airway diseases such as, for example, airway eosinophilia, mucus hypersecretion and airway hyperreactivity. The basis for these diseases are pathophysiological changes during the production of characteristic cytokines by antigen specific TH cells. For instance, transgenic mice which constitutively overexpress the TH2 cytokines IL-4, IL-5, IL-13 or IL-9 in the airway epithelia, show typical allergic inflammatory reactions. In the animal model, TH2 cell subpopulations in the lung and airways induce in TH2 cells the characteristic symptoms of bronchial asthma.

Surprisingly, it was found that transcription factors and factors of signal transduction pathways for differentiation and/or expression of cytokines which are involved in the development of chronic inflammatory reactions and autoimmune diseases, such as, for example, the TH1 cell specific transcription factor T-bet and the TH2 cell specific transcription factor GATA-3, are ideally suited for the cell and/or tissue specific treatment of chronic inflammations or autoimmune diseases.

The TH1 cell specific transcription factor T-bet is, above all, responsible for the differentiation of naive $CD^+$ T cells to TH1 cells. Its expression is controlled by signal transduction pathways of the T cell receptor (TCR) and through INFy receptor/STAT1 T-bet transactivates the endogenous INFy gene and induces the production of INFy. Furthermore, it induces the up-regulation of the protein expression of IL-12Rβ2 chains and leads to chromatin remodelling of individual INFy alleles. The in vivo function of T-bet has been confirmed on knock-out mice (T-bet). Although T-bet deficient mice present a normal lymphocyte development, CD4$^+$T cells from these mice produce no INFy, neither when stimulated with anti-CD3/CD28 nor with PMA/ionomycine. T-bet deficient mice display no immune response to a L. major infection, the amount of TH2 cytokines increases.

The function of T-bet in mucosal T cells during the development of inflammatory bowel diseases is known. Investigations on the animal model show a worsening of colitis in reconstituted SCID (Severe Combined Immunodeficiency) mice after retroviral transduction of T-bet in CD4$^+$CD26L$^+$ T cells, while, conversely, the transfer of T-bet deficient T cells does not lead to an induction of colitis.

The transcription factor T-bet specifically induces the development of TH1 cells and controls the production of INFy in these cells. The inhibition of T-bet shifts the balance between TH1 and TH2 cells towards the TH2 cells.

The TH2 cell specific transcription factor GATA-3 is, above all, responsible for the differentiation of naive CD4$^+$T cells to TH2 cells.

Here, the TH2 cell differentiation is controlled mainly by two signal transmission paths, the T cell receptor (TCR) path and the IL-4 receptor path. Signals forwarded by the TCR activate the TH2 cell specific transcription factors c-Maf and GATA-3 as well as transcription factors NFAT and AP-1. The activation of the IL-4 receptor leads to the binding of STAT6 to the cytoplasmatic domain of the IL-4 receptor, where it is phosphorylated by Jak1 and Jak3 kinases. The phosphorylation leads to dimerisation and translocation of STAT6 into the nucleus, where STAT6 activates the transcription of GATA-3 and other genes. GATA-3 is a zinc finger transcription factor which, according to "Representational Difference Analysis" (RDA) and studies on transcriptional regulation of IL-5, is expressed exclusively in mature TH2 cells and not in TH1 cells. Further transcription factors that play a role in the differentiation to TH1 cells or TH2 cells, respectively, and are involved in the development of chronic inflammatory and autoimmune diseases present an expression which is different in a target cell than compared to a control cell expression and are, according to the present invention, also used in the design of specific DNAzymes and/or siRNA for therapeutic application in chronic inflammatory diseases.

STAT4, STAT5a and STAT1 (signal transducer and activator of transcription)
c-Rel
CREB2 (cAMP response element-binding protein 2)
ATF-2, ATF-2
Hlx
IRF-1 (interferon regulatory factor-1)
c-Maf
NFAT (Nuclear factor of activated T cells)
NIP45 (NF-AT interacting Protein 45)
AP1 (Activator Protein 1)
Mel-18
SKAT-2 (SCAN box, KRAB domain associated with a Th2 phenotype)
CTLA-4 (Cytolytic T lymphocyte-associated antigen 4)

Further factors of the signal transduction pathways that play a role in the differentiation and/or expression of cytokines and are involved in the development of chronic inflammatory and autoimmune diseases exhibit an expression in the target cell that differentiates itself from a control cell expression and are, according to the present invention, also used in the design of specific DNAzymes and/or siRNA for therapeutic application in chronic inflammatory diseases.

Src kinase
Tec kinase
   Rlk (Txk in humans)
   Itk
   Tec
RIBP (Rlk/ltk-binding protein)
PLCγ (Phospholipase Cy1)
MAP kinase (Mitogen-activated protein kinase)
   ERK
   JNK
   P38
MKK (MAP kinase kinase)
   MKK1
   MKK2
   MKK3
   MKK4
   MKK6
   MKK7
Rac2
GADD45 (Growth arrest and DNA damage gene 45)
   GADD45β
   GADD45γ
SOCS (Suppressors of cytokine signalling)
   CIS (Cytokine-induced SH2 protein)
   SOCS1
   SOCS2
   SOCS3
JAK (Janus kinase)
   JAK1
   JAK3
NIP45 (NF-AT interacting Protein 45)

According to the present invention, a cell and/or tissue and/or disease phase specific medicament is provided which is suitable for the treatment of chronic inflammatory diseases.

The medicament acts preferably on the intervention points of the complex cascade of immunological and cell biological defective regulations forming the basis for chronic inflammatory reactions and autoimmune diseases. Particularly preferably, these are intervention points in the regulation of the differentiation of the transcription factors involved, such as, for example, the TH2 cell specific transcription factor GATA-3 or the TH1 cell specific transcription factor T-bet. The therapeutic effect achieved is based on a functional inactivation of ribonucleic acid molecules by means of specific DNAzymes and/or SiRNA. This strategy offers a series of advantages compared to conventional, but also gene therapeutic approaches: highest specificity and selectivity, high stability of the molecules and a negligible antigenicity. Optimal preconditions for a tailored long-term therapy for patients with chronic inflammatory diseases are created.

According to the present invention a method for producing of a cell and/or tissue and/or disease phase specific medicament is provided comprising the steps of:

a) Identification of ribonucleic acid molecules the expression of which is different in a target cell than compared to a control cell expression b) Design of specific ribonucleic acid molecules which bind to ribonucleic acid molecules from step a) and functionally inactivate them c) Introduction of specific ribonucleic acid molecules from step b) into target cells d) Formulation of the specific ribonucleic acid molecules from step b) and/or a target cell from step c) into a medicament In the sense of the present invention, the term "cell and/or tissue and/or disease phase specific" means that the medicament produced by means of the method according to the present invention is substantially only effective in a certain type of cell (target cell) and/or in certain tissues or organs and/or in certain phases of the disease, and has a negligible influence on other cells (control cells) tissues or organs. Preferably the medicament is effective in at least ⅔ of the target cells, more preferably in at least 80% and most preferably on at least 98% of the target cells. It is further preferred that the medicament is effective in no more than 10% of the control cells, more preferred in no more than 5% and most preferred in <1% of the control cells.

In the present invention the term "Identification of ribonucleic acid molecules the expression of which is different in a target cell than compared to a control cell expression" comprises the following points:

i) Target cells are cells in tissues and organs which are known to lead to the development of a disease, contribute thereto or aggravate that disease, which support the processes sustaining the disease, contribute thereto or compound those processes, or which lead to late effects of a disease, contribute thereto or aggravate those effects. They include, for example, cells which present certain transcription factors, secrete specific hormones, cytokines and growth factors, or cells with typical surface receptors.

ii) The target cells can be isolated, for example, by means of technologies which are based on the binding of specific antibodies. Magnetic Beads, obtainable from the companies Miltenyi (Macs-System), Dynal (DynaBeads) or BD-Bioscience (iMAG) are used here. Alternatively, this takes place through cell purification by means of fluorescent labelled antibodies on cell sorters, for example from the company Cytomation (MOFLO) or BD-Bioscience (FACS-Vantage). The purity of the target cells is preferably at least 80%, more preferably at least 95% and most preferably at least 99%.

iii) Methods for isolating RNA are described, e.g. in Sambrook and Russell, Molecular Cloning, A Laboratory Manual, 3. edition, Cold Spring Harbor Laboratory (2001), New York and Ausubel et al., Current Protocols in Molecular Biology, John Wiley & Sons (1998), New York. In addition, it is possible for the average person skilled in the art, to use commercially available kits for RNA isolation (silica technology) e.g. the RNeasy kit from the company Qiagen. It is further preferable to purify mRNA directly from the target cells by using commercial kits, for example from the companies Qiagen (Oligotex mRNA kit), Promega (PolyATract mRNA Isolation System) or Miltenyi (mRNAdirect).

iv) Identification of incrementally different mRNAs, i.e. mRNAs with an expression in the target cell that is higher than the control cell, is conducted, for example, with commercially obtained gene chips (e.g. MWG, CLON-TECH)] or with a filter hybridization method (e.g. Unigene), according to the manufacturer's instructions. Alternatively, differential mRNAs are produced by subtractive hybridization of cDNA which had previously been created from the mRNA through RT reaction. Included in these methods known to the person skilled in the art are, for example, the SSH method (Clontech) or the RDA method. A further preferred application form includes the combination of chip technology and subtractive hybridization. Identification of the differentially expressed genes is carried out using chip technology with the help of commercially available programs, e.g. with the Vector Xpression program from the company InforMax. When using subtractive hybridization, after isolation of the differentially expressed genes by means of conventional methods known to the person skilled in the art, such as cloning and subsequent sequencing (see e.g. Sambrook and Russell, Molecular Cloning, A Laboratory Manual, 3. edition, Cold Spring Harbor Laboratory (2001), New York and Ausubel et al., Current Protocols in Molecular Biology, John Wiley & Sons (1998), New York), a sequence alignment in a data base such as, for example, GenBank (www.ncbi.nlm.nih.gov) is carried out. The expression within the target cell is different compared to the expression in a control cell. In an embodiment of the method according to the present invention the expression in the target cell is higher than the expression in a control cell, preferably at least by a factor 1.5. In a particularly preferred embodiment the expression in the target cell is higher than the expression in a control cell by at least a factor 5, and in a most preferred embodiment the expression is only detectable in the target cell but not in the control cell.

In the sense of the present invention, the term "Design of ribonucleic acid molecules which bind to ribonucleic acid molecules from step a) and functionally inactivate them" comprises the use of RNA inactivating DNA enzymes (DNAzymes) and/or small interfering RNA (siRNA), which functionally inactivates ribonucleic acid molecules.

According to the present invention the term DNAzymes hereby comprises DNA molecules that specifically identify and cleave the target sequence of the nucleic acid, both DNA and RNA.

The "10-23" model represents a general DNAzyme model. DNAzymes of the 10-23 model—also called "10-23 DNAzymes"—possess a catalytic domain of 15 deoxyribonucleic acids, which is flanked by two substrate binding domains. The length of the substrate binding domains is variable, they can either be of the same or of different length. In a preferred embodiment, the substrate binding domains are between 6 and 14 nucleotides long. In a particularly preferred embodiment the substrate binding domains are fully complementary to the region flanking the cleavage site. To bind to and cleave the target RNA, the DNAzyme must not necessarily have to be fully complementary. In vitro investigations show that DNAzymes of the 10-23 type cleave the target RNA at purine-pyrimidine sequences.

To use DNAzymes in the treatment of diseases, preferably, the DNAzymes are stabilized as well as possible against degradation within the body (in the blood, in the intracellular environment, etc.). In a preferred embodiment, a 3'-3' inversion is introduced at one or more ends of the DNAzyme. The term 3'-3' inversion denotes a covalent phosphate bond between the 3' carbon atoms of the terminal nucleotide and the adjacent nucleotide. This type of bond is located, as opposed to the normal phosphate bond, between the 3' and 5' carbon atoms of consecutive nucleotides. Accordingly, it is preferred that the nucleotide on the 3' end is inverse to the of the 3' end of the substrate binding domain adjoining the catalytic domain. In addition to the inversions, DNAzymes can comprise modified nucleotides or nucleotide compounds. Modified nucleotides contain, e.g. N3'-P5' phosphoramidate compounds, 2'-O-methyl substitutions and peptide nucleic acid compounds. Their production is known to the person skilled in the art.

Although the potential DNAzyme cleavage sites occur ubiquitously, they are often blocked by the secondary RNA structure and are thus inaccessible to the DNAzymes. For this reason, only those DNAzymes with freely accessible cleavage sites are selected from a DNAzyme pool. These selected DNAzymes are active, cleave the target mRNA, thus functionally inactivating it. The efficiency of the mRNA cleavage by the individual DNAzymes is shown either by individual testing of each DNAzyme or by coupled testing of multiple DNAzymes in "multiplex assays" (described, e.g. in Cairns et al., 1999).

According to the present invention, the term siRNA comprises 21-23 base long RNA molecules which lead to a specific degradation of the complementary target mRNAs, both in vitro and in vivo. On the basis of the available literature (e.g. http://www.mpibpc.gwdg.de/abteilungen/100/105/index.html), the person skilled in the art is familiar with the production of siRNA molecules starting from the target mRNA sequence. The probability that among three selected siRNA molecules at least one of them is highly active (inhibition of the target RNA by at least 80%), is stated as being at least 70% in the literature. From a pool of siRNA molecules, only those are selected which lead to a specific degeneration of the complementary target mRNA, both in vitro and in vivo.

In the sense of the present invention, the term "introduction of the specific ribonucleic acid molecules from step b) into target cells" comprises the transfection into the target cells of vectors, particularly plasmids, cosmids, viruses or bacteriophages, which contain the previously described specific ribonucleic acid molecules according to the present invention. Preferably, the vectors are suited for transformation of animal and human cells and allow the integration of the ribonucleic acid molecules according to the present invention. Transfection methods such as, for example, lipofection with DMRIE-C from the company Invitrogen are known to the person skilled in the art from the literature. In principle, liposomal vectors are also suited therefor. The target molecules are transcription factors, cells secreting hormones, cytokines and growth factors, but also cells carrying the expressed receptors on the surface. The control cells in the sense of the invention are healthy cells from the target tissue, cells of the same type from other compartments of the same patient or also from healthy individuals.

Cultivation of the target cell is carried out in culture media adapted to the requirements of the target cell in regard to pH value, temperature, salt concentration, antibiotics, vitamins, trace elements and ventilation. The term patient relates equally to humans and vertebrates. The medicament can therefore be used in both human and veterinary medicine.

The term "Formulation of the specific ribonucleic acid molecules from step b) or a target cell from step c) into a medicament" comprises pharmaceutically acceptable compositions containing modifications and "prodrugs", as long as they do not trigger excessive toxicity, irritations or allergic reactions in the patient after conducting a reliable medical assessment. The term "prodrug" relates to compounds which are transformed to improve their absorption, for example, by hydrolysis in the blood.

Preferably, the formulation permits the specific ribonucleic acid molecules to be administered to the patient in form of a pharmaceutically acceptable composition, either orally, rectally, parenterally, intravenously, intramuscularly or subcutaneously, intracisternally, intravaginally, intraperitoneally, intrathecally, intravascularly, locally (powder, ointment or drops) or in spray form.

Dosing forms for local administration of the medicament of this invention comprise ointments, powders, sprays or inhalation means. The active component is admixed under sterile conditions, depending on the requirements, with a physiologically acceptable carrier substance and possible preservatives, buffers or propellants.

The dosing method is determined by the treating physician in accordance with the clinical factors. It is known to the person skilled in the art that the dosing method is dependent on different factors, such as, for example, body size, weight, body surface area, age, sex or the general health of the patient, but also on the specific substance to be administered, the duration and type of administration, and on other medicaments which are possibly administered in parallel.

The medicament produced with the method according to the present invention possesses a high patient, disease, stage and phase specificity. It causes a cell specific intervention and is specific for compartments and organs. No or only very limited reactions of the immune system develop against the medicament and the side effect profile is commensurate with severity index, prognosis and progression of the disease.

The medicament can be used in the therapy of all disease groups associated with chronic inflammations, such as, for example, autoimmune diseases, rheumatic diseases (manifestations on skin, lungs, kidney, vascular system, connective tissue, musculoskeletal system, endocrine system, among other), immediate-type allergic reactions and asthma, chronic obstructive pulmonary diseases (COPD), arteriosclerosis, psoriasis and contact eczema, and also in the therapy of chronic rejection reactions after organ or bone marrow transplant.

EXECUTION EXAMPLES

Example 1

GATA-3 a) Identification of Ribonucleic Acid Molecules the Expression of which is Different in a Target Cell than Compared to a Control Cell Expression i) The naive $CD4^+$ cells responsible for the development of chronic inflammatory reactions are used as target cells.

ii) The $CD4^+$ target cells are isolated using magnetic beads (from Miltenyi (Macs System) Dynal (DynaBeads) or BD-Bioscience (iMAG)), alternatively on cell sorters by means of fluorescent labelled antibodies, e.g. from the companies Cytomation (MOFLO) or BD Bioscience (FACSVantage).

iii) RNA isolation is carried out according to standard methods; see Sambrook and Russell, Molecular Cloning, A Laboratory Manual, 3. edition, Cold Spring Harbor Laboratory (2001), New York and Ausubel et al., Current Protocols in Molecular Biology, John Wiley & Sons (1998), New York.

Alternatively, an RNeasy kit from the company Qiagen is used, or the mRNA is isolated directly from CD4+ target cells using the Oligotex mRNA kit from the company Qiagen, according to manufacturer's instructions.

iv) Identification of incrementally different mRNAs, i.e. mRNAs with a higher expression in the target cell than the control cell, is conducted with gene chips (e.g. MWG, CLON-TECH), and the identification of the differentially expressed genes is carried out by means of the Vector Xpression program from the company InforMax.

Figure 2:
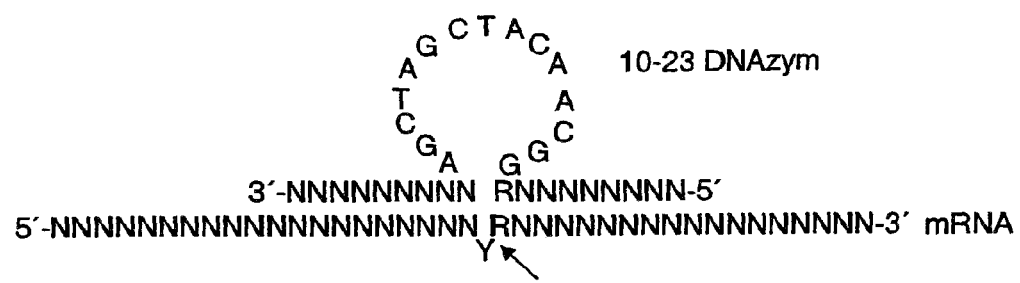
FIG. 2: Nucleotide sequence of the catalytic domain of the 10-23 DNAzyme and binding to a target RNA by means of Watson-Crick pairing. (R=A or G; Y=U or C, N=A, G, U or G). The arrow indicates the cleavage site on the target mRNA.

Filter hybridization method (e.g. Unigene), according to manufacturer's instructions. The isolation of the differentially expressed genes is followed by cloning, sequencing (according to standard procedures, see e.g. Sambrook and Russell, Molecular Cloning, A Laboratory Manual, 3. edition, Cold Spring Harbor Laboratory (2001), and sequence alignment in the gene data base (www.ncbi.nlm.nih.gov). The expression of GATA-3 is different in the target cell (TH2 cell) in comparison with the expression in the control cell (for example Th0 cell).

b) Design of Specific Ribonucleic Acid Molecules which Bind To Ribonucleic Acid Molecules from Step a) and Functionally Inactivate Them FIG. 3 shows the pool hgd 1 to hgd 70 of specific DNAzymes according to the present invention against GATA-3 mRNA. The DNAzymes have a total length of 33 nucleotides, with the central catalytic domain corresponding to 15 nucleotides (in lowercase letters) of the catalytic domain of the known 10-23 DNAzymes (FIG. 2). This catalytic domain is flanked by two right and left substrate binding domains (in uppercase letters), each comprising 9 nucleotides. The nucleotide sequence of the right and left substrate binding domain is different and varies for the DNAzymes hgd 1 to hgd 70, so that a different specific bond takes place by means of Watson-Crick pairing to the GATA-3 mRNA.

FIG. 2 shows the general model for binding the 10-23 DNAzymes to an arbitrary target RNA, labelled N, wherein the arrow points to the cleavage site on the target mRNA. Although DNAzymes can cleave the target mRNA at every purine-pyrimidine sequence, it is known from literature that purine-uracil bonds are cleaved more effectively than purine-cytosine bonds. For this reason, DNAzymes which cleave at purine-uracil bonds are preferably constructed. The model shown in FIG. 2 can be applied, in terms of its operating principle, to the binding of the DNAzymes hgd1 to hgd70 to GATA-3 mRNA.

The DNAzymes hgd1 to hgd70 are used unmodified for in vitro tests and modified for tests on cell cultures (purchased through the company Eurogentec). The following modifications were applied for stabilization and protection:
1) A stabilizing inverse thymidine on the 3' end.
2) a FAM label on the 5' end to assess the transfection efficiency of the cells by means of FACS analysis.

Testing the DNAzymes in vitro requires GATA-3 mRNA that has been produced by in vitro transcription. The individual steps are as follows:
RNA isolation from human EDTA whole blood by means of a QIAamp RNA Blood Mini Kit (Qiagen, Germany), according to manufacturer's instructions.
reverse transcription with the primers:

```
Forward primer          GGCGCCGTCTTGATACTTT
```

Reverse primer CCGAAAATTGAGAGAGAAGGAA, with amplification of a 2731 nucleotide long PCR product (JumpStart Accu Taq DNA polymerase, Sigma).

PCR conditions: Initial denaturation (96° C., 30 sec.), amplification for 40 cycles (94° C., 15 sec.; 48° C., 30 sec.; 68° C., 3 min.), final extension (68° C., 30 min.).

The PCR product is cloned into the plasmid pCR2.1 (Invitrogen) using standard procedures and sequenced for verification. Production of GATA-3 mRNA is carried out after linearization of the GATA-3 containing plasmid pCR2.1 by cleaving with the restriction enzyme Spe I through in vitro transcription according to the manufacturer's instructions (Ambion). GATA-3 mRNA is present with a length of a total of 2876 nucleotides.

FIG. 4 shows the known nucleotide sequences of human GATA-3 genes obtained from database entries [PubMed (http://www.ncbi.nlm.nih.gov/entrez/query.fcgi?db=Nucleotid e)], wherein divergent bases are highlighted in grey. Sequence 1: Human GATA-3 from database no.: XM_043124, sequence 2: Human GATA-3 from database no.: X58072, sequence 3: Human GATA-3 (isolated from plasmid pCR2.1).

The GATA-3 mRNA sequences differentiate themselves from each other by the length of the 3' untranslated or 5' untranslated ends. To obtain the exact complete sequence of the mRNA, the mRNA sequences of the entries no.: XM_043124 and X58072 are used for the primer selection. The primer locations for cloning GATA-3 are highlighted in FIG. 4 by underlining. FIG. 4 also shows an alignment of the nucleic acid sequence of GATA-3 obtained from the data base (sequence 1 and 2) and the nucleotide sequence (sequence 3) sequenced from plasmid pCR2.1. It shows that the sequences are not totally identical, with some bases being different. The nucleic acid sequence 3 of GATA-3 in FIG. 4 forms, according to the present invention, the basis for the construction of DNAzymes against GATA-3 mRNA.

FIG. 4 A shows the nucleotide sequence of sequence 3 of the human GATA-3 gene from FIG. 4 and, drawn therein as grey highlight, two nucleotides GT or AT, respectively, between which there are further potential cleavage sites for DNAzymes.

The in vitro cleavage experiments of GATA-3 mRNA with the DNAzymes (hgd1-hgd70) are conducted in a volume of 10 μl comprising the following reaction composition: 50 mM Tris pH 7.4, 150 mM NaCl, 10 mM $MgCl_2$, 0.25 μM DNAzyme and 0.025 μM GATA-3 mRNA transcribed in vitro (at a substrate to DNAzyme ratio of 1:10). The reactions are incubated at 37° C. for the times indicated for each case. The reaction is stopped by adding formamide and EDTA containing RNA Sample Loading Buffer (Sigma). The denatured samples are separated on 1.3% TAE agarose gels and analyzed in the UV transilluminator.

FIG. 5 shows as the result of the gel electrophoresis the cleavage of the GATA-3 target mRNA with unmodified DNAzymes [hgd11 (lane 2), hgd13 (lane 4), hgd17 (lane 6), hgd40 (lane 8)] and modified DNAzymes [hgd11-M (lane 3), hgd13-M (lane 5), hgd17-M (lane 7), hgd40-M (lane 9)]. Lane 1 contains a control mRNA with no added DNAzyme. The modified DNAzymes are characterized with an additional M. A length standard run in parallel (not shown) shows band sizes of 1000 bp, 2000 by and 3000 bp. The arrows point at S, the band containing the substrate (here GATA-3 mRNA) and the cleavage products P1 and P2.

The comparison between all 70 DNAzymes shows that hgd11, hgd13, hgd17 and hgd40 are particularly active, the modifications lowering the effectiveness of the DNAzyme hgd11, hgd13 and hgd17, but not the effectiveness of the DNAzyme hgd40.

The following table shows the classification of the DNAzyme hgd 1 to hgd 70 against GATA-3 mRNA in 4 groups. This classification is conducted on the basis of in vitro activity tests of the DNAzymes against GATA-3 mRNA. Group 1: high cleavage activity, group 2: average cleavage activity, group 3: weak cleavage activity, and group 4: no measurable cleavage activity.

| Group | Hgd | Activity against GATA-3 |
|---|---|---|
| 1 | 11, 13, 17, 40 | High cleavage activity |
| 2 | 10, 12, 16, 18, 23, 31, 36, 37, 39, 52, 57, 58, 63, 70 | Average cleavage activity |
| 3 | 22, 24, 25, 34, 35, 41, 42, 43, 45, 46, 47, 48, 49, 50, 54, 55, 56, 57 | Weak cleavage activity |
| 4 | 1, 2, 3, 4, 5, 6, 7, 8, 9, 14, 15, 19, 20, 21, 26, 27, 28, 29, 30, 32, 33, 38, 44, 51, 53, 59, 60, 61, 62, 64, 65, 66, 67, 68, 69 | No cleavage activity | c) Introduction of Specific Ribonucleic Acid Molecules from Step b) into Target Cells The highly active DNAzymes hgd11, hgd13, hgd17 and hgd40 are used in target cells with and without the described modifications.

For this, Jurkat E6.1 cells (human acute T cell leukemia cells) are cultivated in the RPMI medium with 100 U/ml penicillin, 0.1 mg/ml streptomycin and 10% FKS at 37° C. in a humidified 5% $CO_2$ atmosphere. The transfections are carried out in 6-well plates. For this, $2 \times 10^6$ Jurkat E6.1 cells are introduced in an Opti-MEM I cell culture medium (Invitrogen) and transfected by means of DMRIE-C (Invitrogen) with the modified DNAzymes (0.3 µM) (according to manufacturer's instructions of the company Invitrogen). After a 10 hour incubation in the incubator under the above-mentioned conditions, the RPMI medium (containing the additions indicated above) is added and the incubation continued for a further 14 hours. The cells are washed with Opti-MEM medium and subsequently transfected again following the protocol described above. The transfection efficiency is assessed after each transfection by means of FACS analysis. The activity of the DNAzymes is subsequently verified by detecting the GATA-3 protein quantity on the Western blot (see FIG. 6).

For Western blot analyses the cytoplasmic proteins and the core proteins are processed separately by means of a protein extraction kit in accordance with manufacturer's instructions (Pierce). The protein concentration is determined with the BCA kit (Pierce). The separation of 30 µg protein in each case is carried out by means of denaturing gel electrophoresis in 10% SDS polyacrylamide gels. The proteins are subsequently blotted on nitrocellulose membranes according to standard procedures. The membranes are blocked with 5% skim milk powder in PBS (with 0.01% Tween 20) and subsequently incubated at room temperature with mouse anti-GATA-3 antibodies (Santa Cruz) (1:500) and following this with HRP-coupled mouse anti-rabbit antibodies (BD Biosciences) (1:2000) for one hour, respectively. The proteins are visualized by means of chemiluminescence. Variations in the protein quantity applied is controlled by parallel detection of beta-actin on the blots. For that, GATA-3 is detected on the nitrocellulose membrane first. The same membrane is subsequently left over night in a humid chamber. After washing with PBS twice, the detection of β-actin takes place through immunostaining with specific antibodies (mouse anti-human beta-actin antibody (Sigma)).

FIG. 6 shows the result of the immunoblot with the resulting activity of the DNAzymes in cells. Jurkat E6.1 cells are transfected by means of lipofection with DNAzymes (lane 4=hgd11-M, lane 5=hgd13-M, lane 6=hgd17-M, lane 7=hgd40-M). Untreated cells (lane 1), cells only treaded with transfection medium (lane 2), and cells treated with DNAzymes and no transfection medium (lane 3) were used for control purposes. After 48 h of incubation, the solubilized proteins are separated by means of SDS-PAGE and GATA-3 (A) detected by immunoblot with specific antibodies. To confirm that the same quantity of protein is being used on each lane, immunostaining with β-actin (B) is carried out on the same blot membrane. A length standard run in parallel (not shown) shows band sizes of 63.8 kDa, 49.5 kDa and 37.4 kDa.

The results show that the DNAzymes hgd11, hgd13 and hgd17 are not active in vivo, while the DNAzyme hgd40 inhibits the GATA-3 expression also in vivo. The specific in vivo inhibition of the GATA-3 expression by the DNAzyme hdg40 hence provides an effective therapeutic tool for the treatment of chronic inflammatory diseases.

d) Formulation of the Specific Ribonucleic Acid Molecules From Step b) and/or a Target Cell from Step c) into a Medicament The analysis of different DNAzymes with a substrate domain specific to GATA-3 shows that the DNAzyme hgd40 specifically inhibits the GATA-3 expression in vivo and is suitable as specific ribonucleic acid for the production of a cell and/or tissue and/or disease phase specific medicament. For this, hgd40 (5'-GTGGATGGAggctagctacaacgaGTCT-TGGAG) or cells transfected with hgd40 are provided in a pharmaceutical composition with a pharmaceutically acceptable carrier for example liposomes or biodegradable polymers.

Alternatively to the DNAzymes, the use of siRNA is proposed for the specific inhibition of the GATA-3 expression and for the production of a cell and/or tissue and/or disease phase specific medicament. Preferably siRNA is used for the inhibition of mouse and human GATA-3. The production of siRNA is known to the person skilled in the art and described in the literature. Examples for siRNA sequences are given below:

| Source | Nucleic acid sequences |
|---|---|
| Mouse GATA-3 | Sense strand: CAUCGAUGGUCAAGGCAACdTdT<br>Antisense strand: GUUGCCUUGACCAUCGAUGdTdT |
| Human GATA-3 sequence 1 | Sense strand: CAUCGAUGGUCAAGGCAACdTdT<br>Antisense strand: GUUGCCUUGACCGUCGAUGdTdT |
| Human GATA-3 sequence 2 | Sense strand: AAGAGUGCCUCAAGUACCAdTdT<br>Antisense strand: UGGUACUUGAGGCACUCUUdTdT |
| Human GATA-3 sequence 3 | Sense strand: AGCUUCACAAUAUUAACAGdTdT<br>Antisense strand: CUGUUAAUAUUGUGAAGCUdTdT |
| Human GATA-3 sequence 4 | Sense strand: UGACUCACUGGAGGACUUCdTdT<br>Antisense strand: GAAGUCCUCCAGUGAGUCAdTdT |

Example 2

DNAzyme Against T-bet a) Identification of Ribonucleic Acid Molecules the Expression of which is Different in a Target Cell than Compared to a Control Cell Expression The identification takes place according to the procedure described above. The expression of T-bet is different in the target cell (Th1 cell) in comparison with the expression in a control cell (Th0 cell).

b) Design of Specific Ribonucleic Acid Molecules which Bind To Ribonucleic Acid Molecules from Step a) and Functionally Inactivate Them The identification of cleavage sites for cleavage of T-bet is carried out as described for GATA-3.

FIG. 7 shows the pool td1-td78 of specific DNAzymes according to the present invention against T-bet mRNA. The DNAzymes have a total length of 33 nucleotides, with the central catalytic domain corresponding to 15 nucleotides (in lowercase letters) of the catalytic domain of the known 10-23 DNAzyme (FIG. 2). This catalytic domain is flanked by two right and left substrate binding domains (in uppercase letters), each comprising 9 nucleotides. The nucleotide sequence of the right and left substrate binding domain is different and varies for the DNAzymes td1 to td78, so that a different specific bond takes place by means of Watson-Crick pairing to the T-bet mRNA.

Since it is known from literature that DNAzymes cleave the target mRNA at purine-uracil more effectively than at purine-cytosine bonds, DNAzymes which cleave at purine-uracil bonds are preferably constructed.

The model shown in FIG. 2 can be applied, in terms of its operating principle, to the binding of the DNAzymes td1 to td78 to T-bet mRNA.

The DNAzymes td1 to td78 are used unmodified for in vitro tests and with the modifications described for GATA-3 for tests on cell cultures.

To present the cleavage properties of the DNAzymes and the functional inactivation of the target mRNA of the T-bet mRNA, in vitro transcription of the T-bet mRNA from human EDTA whole blood is carried out by means of a QIAamp RNA Blood Mini Kit (Qiagen, Germany), according to manufacturer's instructions.

FIG. 8 shows the nucleotide sequence of human T-bet, as obtained from the database entries [PubMed (http://www.ncbi.nlm.nih.gov/entrez/query.fcgi?db=Nucleotid e)] no.: NM_013351, sequence 1.

The reverse transcription takes place with the forward primer CGGCCCGCTGGAGAGGAAGC and reverse primer CACACACCCACACACAACC in accordance with standard procedures (ThermoScript from Invitrogen), with amplification of a 2450 nucleotide long PCR product. This PCR product is cloned into the pBluescript-SK (Stratagene) using standard procedures and sequenced for verification.

FIG. 8 shows a comparison between the nucleic acid sequence of T-bet no.: NM_013351 (sequence 1) and the sequenced sequence (sequence 2). It shows that the sequences are not totally identical, with individual bases being interchanged. The nucleic acid sequence 2 of T-bet in FIG. 8 forms, according to the present invention, the basis for the construction of DNAzymes against T-bet mRNA.

FIG. 8A shows the nucleotide sequence of sequence 1 of the human T-bet gene from FIG. 8 and, drawn therein with grey highlight, two nucleotides GT or AT, respectively, between which there are further potential cleavage sites for DNAzymes.

Production of T-bet mRNA is carried out after linearization of the T-bet containing plasmid pBluescript-SK by cleaving with the restriction enzyme Xba I (Fermentas) and through in vitro transcription according to the manufacturer's instructions (Ambion). T-bet mRNA is present with a length of a total of 2550 nucleotides.

The in vitro cleavage experiments of T-bet mRNA with the DNAzymen (td1 to td78) are conducted and analyzed in accordance with the descriptions to GATA-3. FIG. 9 shows as the result of the gel electrophoresis the cleavage of the T-bet target mRNA with modified DNAzymes [td54-M (lane 3), td69-M (lane 4), td70-M (lane 5)]. Lane 2 contains a control T-bet mRNA with no added DNAzyme. A length standard run in parallel (lane M) shows band sizes of 2000 by and 3000 bp. The arrows point at A, the band containing the substrate (here T-bet mRNA) and B, one of the two cleavage products (the other cleavage product is not shown in this figure).

The comparison between all 78 DNAzymes shows that td54, td69 and td70 are particularly active, the modifications not decreasing the effectiveness of the DNAzyme.

The following table shows the classification of the DNAzyme td 1 to td78 against t-bet-3 mRNA in 4 groups. This classification is conducted on the basis of in vitro activity tests of the DNAzymes against t-bet mRNA. Group 1: high cleavage activity, group 2: average cleavage activity, group 3: weak cleavage activity, and group 4: no measurable cleavage activity.

| Group | Td | Activity against t-bet mRNA |
|---|---|---|
| 1 | 54, 69, 70 | High cleavage activity |
| 2 | 21, 24, 28, 29, 30, 45, 71, 72, 77, 78 | Average cleavage activity |
| 3 | 13, 19, 22, 23, 25, 27, 31, 32, 44, 46, 47, 48, 50, 51, 53, 55, 56, 57, 58, 60, 61, 62, 65, 67, 68, 73, 74, 75 | Weak cleavage activity |
| 4 | 1, 2, 3, 4, 5, 6, 7, 8, 9, 10, 11, 12, 14, 15, 16, 17, 18, 20, 26, 33, 34, 35, 36, 37, 38, 39, 40, 41, 42, 43, 49, 52, 59, 63, 64, 66, 76 | No cleavage activity | c) Introduction of Specific Ribonucleic Acid Molecules from Step b) into Target Cells The DNAzymes td54, td69 and td70 are used in target cells with and without the described modifications. The data on the transfection of Jurkat E6.1 cells corresponds that on the execution example GATA-3. After transfection of Jurkat E6.1 cells the quantity of T-bet mRNA relative to GAPDH mRNA expression is determined quantitatively by means of real-time PCR (LightCycler, Roche) to obtain information on the in vitro effectiveness of the DNAzymes.

For LightCycler analyses the RNA from the Jurkat E6.1 cells is purified by means of RNeasy Mini Kit (Qiagen, Germany) and subsequently normalized photometrically. After reverse transcription with SuperScript II (Gibco) in accordance with manufacturer's instructions follows the quantitative analysis of the T-bet mRNA and GAPDH mRNA in the LightCycler. The total volume for the PCR is of 20 µl, containing 1 µl DNA, 1 µl (0.5 µM) for each the sense and the antisense primer, as well as 10 µl QuantiTect SYBR Green PCR Master Mix (Qiagen, Germany). The PCR primers used for T-bet are: Sense 5'-CCCACCATGTCCTACTACCG-3'; Antisense 5'-GCAATCTCAGTCCACACCAA-3'. The PCR primers used for GAPDH are: Sense 5'-CCCACCATGTC-CTACTACCG-3'; Antisense 5'-GCAATCTCAGTCCACAC-CAA-3'. The PCR conditions are: Denaturation (15 min 95° C.), amplification (15 sec 95° C., 25 sec 59° C., 25 sec 72° C. for 50 cycles) then final extension 2 min 72° C. The following melting curve is generated as follows: 0 sec 95° C., 15 sec 60° C. then increase the temperature to ° C. in 0.2° C. increments, simultaneously measuring the fluorescence. The melting curve is used for internal control since all PCR products have a specific melting temperature.

SYBR Green is a fluorescent dye (included in the Quanti-Tect SYBR Green PCR Master Mix) that binds double stranded DNA. When the DNA is doubled during the extension, SYBR Green binds to it generating a bond dependent fluorescence signal which is detected by the LightCycler at the end of every extension. The higher the quantity of initial material, the earlier a significant increase in the fluorescence will be detected. The LightCycler software provides a graphical representation of the collected fluorescence intensities against the cycles.

FIG. 10 shows LightCycler amplification curves of T-bet mRNA and GAPDH mRNA after treatment of Jurkat E6.1 cells with the DNAzymes td54m, td69m and td70m in comparison to those treated with nonsense-DNAzyme. The individual crossing point (Ct), defined as the PCR cycle at which the fluorescence first distinguishes itself significantly from the background fluorescence, is determined manually with the fit point method of the LightCycler software. The relative quantification of T-bet mRNA and GAPDH mRNA in cells treated with DNAzymes compared with cells treated with nonsense DNAzyme is carried out according to the instructions described in the User Bulletin #2 (ABI Prism 7700 Sequence detection System User Bulletin #2 (2001) Relative quantification of gene expression http://docs.appliedbiosystems.com/pebiodocs/04303859.pdf). Here, the quantity of T-bet mRNA from the control test is set equal to 100%. The data from the relative quantification are represented graphically in FIG. 11.

Compared to nonsense DNAzyme treatment, it is shown that the td69m DNAzyme leads to a suppression of 81.3% and the td70m DNAzyme to a suppression of 81.0%, while the td54m DNAzyme has no suppressive effect on T-bet mRNA.

This means that the td54m DNAzyme is not active in vivo, while td69m and td70m DNAzymes inactivate the mRNA of T-bet also in the cellular environment. The specific in vivo reduction of the T-bet mRNA by the DNAzyme td69m and td70m hence provides an effective therapeutic tool for the treatment of chronic inflammatory diseases.

d) Formulation of the Specific Ribonucleic Acid Molecules from Step b) and/or a Target Cell from Step c) into a Medicament The analysis of different DNAzymes with a substrate domain specific to T-bet shows that DNAzymes td69 and td70 specifically inhibit the T-bet expression in vivo and are suitable as specific ribonucleic acid for the production of a cell and/or tissue and/or disease phase specific medicament.

For this, td69 (GGCAATGAAggctagctacaacgaTGGGTTTCT) or td70 (TCACGGCAAggctagctacaacgaGAACTGGGT) or cells transfected with td69m or td70, respectively, are provided in a pharmaceutical composition with a pharmaceutically acceptable carrier for example liposomes or biodegradable polymers.

Alternatively to the DNAzymes, the use of siRNA is proposed for the specific inhibition of the T-bet expression and for the production of a cell and/or tissue and/or disease phase specific medicament. Preferably this is siRNA for inhibiting human T-bet. The production of siRNA is known to the person skilled in the art and described in the literature. The following is an example for siRNA sequences:

| Source | Nucleic acid sequences |
|---|---|
| Human T-bet | Sense strand: UCAGCACCAGACAGAGAUGdTdT Antisense strand: CAUCUCUGUCUGGUGCUGAdTdT |

It is evident to the person skilled in the art that with the teachings of the present invention specific DNAzymes and siRNAs can also be easily produced as medicament for chronic inflammatory diseases and autoimmune diseases, which are directed against further transcription factors that play a role in the differentiation to TH1 or TH2 cells, respectively, for example STAT4, STAT5a, STAT1, c-Rel, CREB2, ATF-2, Hlx, IRF-1, c-Maf, NFAT, NIP45, AP1, Mel-18, SKAT-2, CTLA-4 or which are directed against further factors of the signal transduction pathways for differentiation and/or expression of cytokines, for example Src kinase, Tec kinase, Rlk (Txk in humans), ltk, Tec, RIBP, PLCy, MAP kinase, ERK, JNK, P38, MKK, MKK1, MKK2, MKK3, MKK4, MKK6, MKK7, Rac2, GADD45, GADD45β, GADD45y, SOCS, CIS, SOCS1, SOCS2, SOCS3, JAK, JAK1, JAK3, NIP45.

These Proteins present an expression which is higher in a target cell when compared to the expression in a control cell.

SEQUENCE LISTING

<160> NUMBER OF SEQ ID NOS: 154

<210> SEQ ID NO 1
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd1 DNAzyme against GATA-3mRNA

<400> SEQUENCE: 1
tcggtcagag gctagctaca acgatgcgtt gct                33

<210> SEQ ID NO 2
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hdg2 DNAzyme against GATA-3mRNA

<400> SEQUENCE: 2
ggcgtacgag gctagctaca acgactgctc ggt                33

```
<210> SEQ ID NO 3
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd3 DNAzyme against GATA-3mRNA

<400> SEQUENCE: 3
ggcggcgtag gctagctaca acgagacctg ctc                                33

<210> SEQ ID NO 4
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd4 DNAzyme against GATA-3mRNA

<400> SEQUENCE: 4
ctcgggtcag gctagctaca acgactgggt agc                                33

<210> SEQ ID NO 5
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd5 DNAzyme against GATA-3mRNA

<400> SEQUENCE: 5
tcctctgcag gctagctaca acgacggggt cct                                33

<210> SEQ ID NO 6
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd6 DNAzyme against GATA-3mRNA

<400> SEQUENCE: 6
actctgcaag gctagctaca acgatctgcg agc                                33

<210> SEQ ID NO 7
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd7 DNAzyme against GATA-3mRNA

<400> SEQUENCE: 7
gggcgacgag gctagctaca acgatctgca att                                33

<210> SEQ ID NO 8
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd8 DNAzyme against GATA-3mRNA
```

<400> SEQUENCE: 8
aaggggcgag gctagctaca acgagactct gca                                    33

<210> SEQ ID NO 9
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd9 DNAzyme against GATA-3mRNA

<400> SEQUENCE: 9
aaaacgggag gctagctaca acgacaggtt gta                                    33

<210> SEQ ID NO 10
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd10 DNAzyme against GATA-3mRNA

<400> SEQUENCE: 10
agaataaaag gctagctaca acgagggacc agg                                    33

<210> SEQ ID NO 11
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd11 DNAzyme against GATA-3mRNA

<400> SEQUENCE: 11
atggcagaag gctagctaca acgaaaaacg gga                                    33

<210> SEQ ID NO 12
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd12 DNAzyme against GATA-3mRNA

<400> SEQUENCE: 12
aactgggtag gctagctaca acgaggcaga ata                                    33

<210> SEQ ID NO 13
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd13 DNAzyme against GATA-3mRNA

<400> SEQUENCE: 13
atccaaaaag gctagctaca acgatgggta tgg                                    33

<210> SEQ ID NO 14
<211> LENGTH: 33
<212> TYPE: DNA
<213> ORGANISM: Homo sapiens
<220> FEATURE:

```
<221> NAME/KEY: misc_feature
<222> LOCATION: (1)..(33)
<223> OTHER INFORMATION: hgd14 DNAzyme against GATA-3mRNA

<400> SEQUENCE: 14
aggggaagag gctagctaca acgaaaaaat cca                                       33

<210> SEQ ID NO 15
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd15 DNAzyme against GATA-3mRNA

<400> SEQUENCE: 15
ttttaaaaag gctagctaca acgatatctt gga                                       33

<210> SEQ ID NO 16
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd16 DNAzyme against GATA-3mRNA

<400> SEQUENCE: 16 gtgggggag gctagctaca acgagggaag gct                                        33

<210> SEQ ID NO 17
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd17 DNAzyme against GATA-3mRNA

<400> SEQUENCE: 17
gttgaatgag gctagctaca acgattgctt tcg                                       33

<210> SEQ ID NO 18
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd18 DNAzyme against GATA-3mRNA

<400> SEQUENCE: 18
gtcgttgaag gctagctaca acgagatttg ctt                                       33

<210> SEQ ID NO 19
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd19 DNAzyme against GATA-3mRNA

<400> SEQUENCE: 19
ggcccggaag gctagctaca acgaccgcgc gcg                                       33

<210> SEQ ID NO 20
```

```
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd20 DNAzyme against GATA-3mRNA

<400> SEQUENCE: 20
tcacctccag gctagctaca acgaggcctc ggc                                33

<210> SEQ ID NO 21
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd21 DNAzyme against GATA-3mRNA

<400> SEQUENCE: 21
ccgccgtcag gctagctaca acgactccat ggc                                33

<210> SEQ ID NO 22
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd22 DNAzyme against GATA-3mRNA

<400> SEQUENCE: 22
ggtggctcag gctagctaca acgaccagcg cgg                                33

<210> SEQ ID NO 23
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd23 DNAzyme against GATA-3mRNA

<400> SEQUENCE: 23
cgttgagcag gctagctaca acgaggcggg gtg                                33

<210> SEQ ID NO 24
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd24 DNAzyme against GATA-3mRNA

<400> SEQUENCE: 24
ccgcgtccag gctagctaca acgagtagga gtg                                33

<210> SEQ ID NO 25
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd25 DNAzyme against GATA-3mRNA

<400> SEQUENCE: 25
```
cagcgggtag gctagctaca acgatgcgcc gcg                                    33

<210> SEQ ID NO 26
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd26 DNAzyme against GATA-3mRNA

<400> SEQUENCE: 26
gcacatccag gctagctaca acgactcctc cgg                                    33

<210> SEQ ID NO 27
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd27 DNAzyme against GATA-3mRNA

<400> SEQUENCE: 27
aaaagcacag gctagctaca acgaccacct cct                                    33

<210> SEQ ID NO 28
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd28 DNAzyme against GATA-3mRNA

<400> SEQUENCE: 28
taaaaagcag gctagctaca acgaatccac ctc                                    33

<210> SEQ ID NO 29
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd29 DNAzyme against GATA-3mRNA

<400> SEQUENCE: 29
gaccgtcgag gctagctaca acgagttaaa aag                                    33

<210> SEQ ID NO 30
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd30 DNAzyme against GATA-3mRNA

<400> SEQUENCE: 30
ttgccttgag gctagctaca acgacgtcga tgt                                    33

<210> SEQ ID NO 31
<211> LENGTH: 33
<212> TYPE: DNA
<213> ORGANISM: Homo sapiens
<220> FEATURE:
<221> NAME/KEY: misc_feature
<222> LOCATION: (1)..(33)

<223> OTHER INFORMATION: hgd31 DNAzyme against GATA-3mRNA

<400> SEQUENCE: 31
agggcgggag gctagctaca acgagtggtt gcc                                33

<210> SEQ ID NO 32
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd32 DNAzyme against GATA-3mRNA

<400> SEQUENCE: 32
tggccctgag gctagctaca acgacgagtt tcc                                33

<210> SEQ ID NO 33
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd33 DNAzyme against GATA-3mRNA

<400> SEQUENCE: 33
acctctgcag gctagctaca acgacgtggc cct                                33

<210> SEQ ID NO 34
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd34 DNAzyme against GATA-3mRNA

<400> SEQUENCE: 34
cggagggtag gctagctaca acgactctgc acc                                33

<210> SEQ ID NO 35
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd35 DNAzyme against GATA-3mRNA

<400> SEQUENCE: 35
ggcggcacag gctagctaca acgactggct ccc                                33

<210> SEQ ID NO 36
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd36 DNAzyme against GATA-3mRNA

<400> SEQUENCE: 36
cgggcggcag gctagctaca acgaacctgg ctc                                33

<210> SEQ ID NO 37
<211> LENGTH: 33
<212> TYPE: DNA

```
<213> ORGANISM: Homo sapiens
<220> FEATURE:
<221> NAME/KEY: misc_feature
<222> LOCATION: (1)..(33)
<223> OTHER INFORMATION: hgd37 DNAzyme against GATA-3mRNA

<400> SEQUENCE: 37
agggatccag gctagctaca acgagaagca gag                                  33

<210> SEQ ID NO 38
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd38 DNAzyme against GATA-3mRNA

<400> SEQUENCE: 38
gggtagggag gctagctaca acgaccatga agc                                  33

<210> SEQ ID NO 39
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd39 DNAzyme against GATA-3mRNA

<400> SEQUENCE: 39
gggctgagag gctagctaca acgatccagg ggg                                  33

<210> SEQ ID NO 40
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd40 DNAzyme against GATA-3mRNA

<400> SEQUENCE: 40
gtggatggag gctagctaca acgagtcttg gag                                  33

<210> SEQ ID NO 41
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd 41 DNAzyme against GATA-3mRNA

<400> SEQUENCE: 41
cgtggtggag gctagctaca acgaggacgt ctt                                  33

<210> SEQ ID NO 42
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd 42 DNAzyme against GATA-3mRNA

<400> SEQUENCE: 42
gggggtagag gctagctaca acgaggagag ggg                                  33
```

```
<210> SEQ ID NO 43
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd 43 DNAzyme against GATA-3mRNA

<400> SEQUENCE: 43
ggaggaggag gctagctaca acgagaggcc ggg                                33

<210> SEQ ID NO 44
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd44 DNAzyme against GATA-3mRNA

<400> SEQUENCE: 44 gcccccccgag gctagctaca acgaaaggag gag                               33

<210> SEQ ID NO 45
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd45 DNAzyme against GATA-3mRNA

<400> SEQUENCE: 45
ccggggagag gctagctaca acgagtcctt cgg                                33

<210> SEQ ID NO 46
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd46 DNAzyme against GATA-3mRNA

<400> SEQUENCE: 46
ggacagcgag gctagctaca acgagggtcc ggg                                33

<210> SEQ ID NO 47
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd47 DNAzyme against GATA-3mRNA

<400> SEQUENCE: 47
tggggtggag gctagctaca acgaagcgat ggg                                33

<210> SEQ ID NO 48
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd48 DNAzyme against GATA-3mRNA
```

```
<400> SEQUENCE: 48
cttgaggcag gctagctaca acgatctttc tcg                                    33

<210> SEQ ID NO 49
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd49 DNAzyme against GATA-3mRNA

<400> SEQUENCE: 49
cacctggtag gctagctaca acgattgagg cac                                    33

<210> SEQ ID NO 50
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd50 DNAzyme against GATA-3mRNA

<400> SEQUENCE: 50 gcagggcag gctagctaca acgactggta ctt                                     33

<210> SEQ ID NO 51
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd51 DNAzyme against GATA-3mRNA

<400> SEQUENCE: 51
ccagcttcag gctagctaca acgagctgtc ggg                                    33

<210> SEQ ID NO 52
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd52 DNAzyme against GATA-3mRNA

<400> SEQUENCE: 52
gtgggacgag gctagctaca acgatccagc ttc                                    33

<210> SEQ ID NO 53
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd53 DNAzyme against GATA-3mRNA

<400> SEQUENCE: 53
ggagtgggag gctagctaca acgagactcc agc                                    33

<210> SEQ ID NO 54
<211> LENGTH: 33
<212> TYPE: DNA
<213> ORGANISM: Homo sapiens
<220> FEATURE:
```

<221> NAME/KEY: misc_feature
<222> LOCATION: (1)..(33)
<223> OTHER INFORMATION: hgd54 DNAzyme against GATA-3mRNA

<400> SEQUENCE: 54
atgctgccag gctagctaca acgagggagt ggg                          33

<210> SEQ ID NO 55
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd55 DNAzyme against GATA-3mRNA

<400> SEQUENCE: 55
gggcggtcag gctagctaca acgagctgcc acg                          33

<210> SEQ ID NO 56
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd56 DNAzyme against GATA-3mRNA

<400> SEQUENCE: 56
gaggctccag gctagctaca acgaccaggg cgg                          33

<210> SEQ ID NO 57
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd57 DNAzyme against GATA-3mRNA

<400> SEQUENCE: 57
gtgggtcgag gctagctaca acgagaggag gct                          33

<210> SEQ ID NO 58
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd58 DNAzyme against GATA-3mRNA

<400> SEQUENCE: 58
aggtggtgag gctagctaca acgaggggtg gtg                          33

<210> SEQ ID NO 59
<211> LENGTH: 33
<212> TYPE: DNA
<213> ORGANISM: Homo sapiens
<220> FEATURE:
<221> NAME/KEY: Misc_feature
<222> LOCATION: (1)..(33)
<223> OTHER INFORMATION: hgd59 DNAzyme against GATA-3mRNA

<400> SEQUENCE: 59
actcgggcag gctagctaca acgagtaggg cgg                          33

<210> SEQ ID NO 60

```
<211> LENGTH: 33
<212> TYPE: DNA
<213> ORGANISM: Homo sapiens
<220> FEATURE:
<221> NAME/KEY: misc_feature
<222> LOCATION: (1)..(33)
     <223 >hgd60 DNAzyme against GATA-3mRNA

<400> SEQUENCE: 60
ggagctgtag gctagctaca acgatcgggc acg                                 33

<210> SEQ ID NO 61
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd61 DNAzyme against GATA-3mRNA

<400> SEQUENCE: 61
ggacttgcag gctagctaca acgaccgaag ccg                                 33

<210> SEQ ID NO 62
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd62 DNAzyme against GATA-3mRNA

<400> SEQUENCE: 62
gggcctggag gctagctaca acgattgcat ccg                                 33

<210> SEQ ID NO 63
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd63 DNAzyme against GATA-3mRNA

<400> SEQUENCE: 63
tgtgctggag gctagctaca acgacgggcc ttg                                 33

<210> SEQ ID NO 64
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd64 DNAzyme against GATA-3mRNA

<400> SEQUENCE: 64
gttcacacag gctagctaca acgatccctg cct                                 33

<210> SEQ ID NO 65
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd65 DNAzyme against GATA-3mRNA

<400> SEQUENCE: 65
```
cagttcacag gctagctaca acgaactccc tgc                                    33

<210> SEQ ID NO 66
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd66 DNAzyme against GATA-3mRNA

<400> SEQUENCE: 66
cacagttcag gctagctaca acgaacactc cct                                    33

<210> SEQ ID NO 67
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd67 DNAzyme against GATA-3mRNA

<400> SEQUENCE: 67
gttgccccag gctagctaca acgaagttca cac                                    33

<210> SEQ ID NO 68
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd68 DNAzyme against GATA-3mRNA

<400> SEQUENCE: 68
tcgccgccag gctagctaca acgaagtggg gtc                                    33

<210> SEQ ID NO 69
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd69 DNAzyme against GATA-3mRNA

<400> SEQUENCE: 69
cccgtgccag gctagctaca acgactcgcc gcc                                    33

<210> SEQ ID NO 70
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd70 DNAzyme against GATA-3mRNA

<400> SEQUENCE: 70
ggcgttgcag gctagctaca acgaaggtag tgt                                    33

<210> SEQ ID NO 71
<211> LENGTH: 33
<212> TYPE: DNA
<213> ORGANISM: Homo sapiens
<220> FEATURE:
<221> NAME/KEY: misc_feature
<222> LOCATION: (1)..(33)

<223> OTHER INFORMATION: td1 DNAzyme against T-bet mRNA

<400> SEQUENCE: 71
tggcttctag gctagctaca acgagccctc gtc					33

<210> SEQ ID NO 72
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td2 DNAzyme against T-bet mRNA

<400> SEQUENCE: 72
gggctctgag gctagctaca acgagcctgg ctt					33

<210> SEQ ID NO 73
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td3 DNAzyme against T-bet mRNA

<400> SEQUENCE: 73
gggaccccag gctagctaca acgacggagc ccg					33

<210> SEQ ID NO 74
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td4 DNAzyme against T-bet mRNA

<400> SEQUENCE: 74
ggtgggggag gctagctaca acgacccacc gga					33

<210> SEQ ID NO 75
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td5 DNAzyme against T-bet mRNA

<400> SEQUENCE: 75 ggcggggag gctagctaca acgaccgagg gcc					33

<210> SEQ ID NO 76
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td6 DNAzyme against T-bet mRNA

<400> SEQUENCE: 76
gggctgggag gctagctaca acgagggcag gga					33

<210> SEQ ID NO 77
<211> LENGTH: 33
<212> TYPE: DNA

<213> ORGANISM: Homo sapiens
<220> FEATURE:
<221> NAME/KEY: misc_feature
<222> LOCATION: (1)..(33)
<223> OTHER INFORMATION: td7 DNAzyme against T-bet mRNA

<400> SEQUENCE: 77
cgtcgaggag gctagctaca acgaccgccc ctc         33

<210> SEQ ID NO 78
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td8 DNAzyme against T-bet mRNA

<400> SEQUENCE: 78
gggctggcag gctagctaca acgacttccc gta         33

<210> SEQ ID NO 79
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td9 DNAzyme against T-bet mRNA

<400> SEQUENCE: 79
cgatgcccag gctagctaca acgaccgggg cgg         33

<210> SEQ ID NO 80
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td10 DNAzyme against T-bet mRNA

<400> SEQUENCE: 80
gctccacgag gctagctaca acgagcccat ccg         33

<210> SEQ ID NO 81
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td11 DNAzyme against T-bet mRNA

<400> SEQUENCE: 81
ccggctccag gctagctaca acgagatgcc cat         33

<210> SEQ ID NO 82
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td12 DNAzyme against T-bet mRNA

<400> SEQUENCE: 82
tctccgcaag gctagctaca acgaccggct cca         33

<210> SEQ ID NO 83
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td13 DNAzyme against T-bet mRNA

<400> SEQUENCE: 83
ccgtcagcag gctagctaca acgagtctcc gca                                33

<210> SEQ ID NO 84
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td14 DNAzyme against T-bet mRNA

<400> SEQUENCE: 84
tccccggcag gctagctaca acgacggctc ggt                                33

<210> SEQ ID NO 85
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td15 DNAzyme against T-bet mRNA

<400> SEQUENCE: 85
cccccgcgag gctagctaca acgagctcgt ccg                                33

<210> SEQ ID NO 86
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td16 DNAzyme against T-bet mRNA

<400> SEQUENCE: 86
gtagggagag gctagctaca acgacccagg ctg                                33

<210> SEQ ID NO 87
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td17 DNAzyme against T-bet mRNA

<400> SEQUENCE: 87
gggcgggcag gctagctaca acgacaaggc gcc                                33

<210> SEQ ID NO 88
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td18 DNAzyme against T-bet mRNA

```
<400> SEQUENCE: 88
cgggaaggag gctagctaca acgatcgccc gcg                                  33

<210> SEQ ID NO 89
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td19 DNAzyme against T-bet mRNA

<400> SEQUENCE: 89
tagtcctcag gctagctaca acgagcggcc ccg                                  33

<210> SEQ ID NO 90
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td20 DNAzyme against T-bet mRNA

<400> SEQUENCE: 90
tccccgacag gctagctaca acgactccag tcc                                  33

<210> SEQ ID NO 91
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td21 DNAzyme against T-bet mRNA

<400> SEQUENCE: 91
tttccccgag gctagctaca acgaacctcc agt                                  33

<210> SEQ ID NO 92
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td22 DNAzyme against T-bet mRNA

<400> SEQUENCE: 92
tgagcgcgag gctagctaca acgacctcag ttt                                  33

<210> SEQ ID NO 93
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td23 DNAzyme against T-bet mRNA

<400> SEQUENCE: 93
ggaccacaag gctagctaca acgaaggtgg ttg                                  33

<210> SEQ ID NO 94
<211> LENGTH: 33
<212> TYPE: DNA
<213> ORGANISM: Homo sapiens
<220> FEATURE:
```

```
<221> NAME/KEY: misc_feature
<222> LOCATION: (1)..(33)
<223> OTHER INFORMATION: td24 DNAzyme against T-bet mRNA

<400> SEQUENCE: 94
cttggaccag gctagctaca acgaaacagg tgg                              33

<210> SEQ ID NO 95
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td25 DNAzyme against T-bet mRNA

<400> SEQUENCE: 95
aaacttggag gctagctaca acgacacaac agg                              33

<210> SEQ ID NO 96
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td26 DNAzyme against T-bet mRNA

<400> SEQUENCE: 96
ctgattaaag gctagctaca acgattggac cac                              33

<210> SEQ ID NO 97
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td27 DNAzyme against T-bet mRNA

<400> SEQUENCE: 97
tggtgctgag gctagctaca acgataaact tgg                              33

<210> SEQ ID NO 98
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td28 DNAzyme against T-bet mRNA

<400> SEQUENCE: 98
tgatgatcag gctagctaca acgactctgt ctg                              33

<210> SEQ ID NO 99
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td29 DNAzyme against T-bet mRNA

<400> SEQUENCE: 99
tggtgatgag gctagctaca acgacatctc tgt                              33

<210> SEQ ID NO 100
```

<210> SEQ ID NO 100
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td30 DNAzyme against T-bet mRNA

<400> SEQUENCE: 100
gcttggtgag gctagctaca acgagatcat ctc                    33

<210> SEQ ID NO 101
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td31 DNAzyme against T-bet mRNA

<400> SEQUENCE: 101
atgggaacag gctagctaca acgaccgccg tcc                    33

<210> SEQ ID NO 102
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td32 DNAzyme against T-bet mRNA

<400> SEQUENCE: 102
gaatgggaag gctagctaca acgaatccgc cgt                    33

<210> SEQ ID NO 103
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td33 DNAzyme against T-bet mRNA

<400> SEQUENCE: 103
tgacaggaag gctagctaca acgagggaac atc                    33

<210> SEQ ID NO 104
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td34 DNAzyme against T-bet mRNA

<400> SEQUENCE: 104
agtaaatgag gctagctaca acgaaggaat ggg                    33

<210> SEQ ID NO 105
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td35 DNAzyme against T-bet mRNA

<400> SEQUENCE: 105

-continued cacagtaaag gctagctaca acgagacagg aat                                    33

<210> SEQ ID NO 106
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td36 DNAzyme against T-bet mRNA

<400> SEQUENCE: 106
gcccggccag gctagctaca acgaagtaaa tga                                    33

<210> SEQ ID NO 107
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td37 DNAzyme against T-bet mRNA

<400> SEQUENCE: 107
ccacaaacag gctagctaca acgacctgta gtg                                    33

<210> SEQ ID NO 108
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td38 DNAzyme against T-bet mRNA

<400> SEQUENCE: 108
gtccacaaag gctagctaca acgaatcctg tag                                    33

<210> SEQ ID NO 109
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td39 DNAzyme against T-bet mRNA

<400> SEQUENCE: 109
ccacgtccag gctagctaca acgaaaacat cct                                    33

<210> SEQ ID NO 110
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td40 DNAzyme against T-bet mRNA

<400> SEQUENCE: 110
ccaagaccag gctagctaca acgagtccac aaa                                    33

<210> SEQ ID NO 111
<211> LENGTH: 33
<212> TYPE: DNA
<213> ORGANISM: Homo sapiens
<220> FEATURE:
<221> NAME/KEY: misc_feature
<222> LOCATION: (1)..(33)

<223> OTHER INFORMATION: td41 DNAzyme against T-bet mRNA

<400> SEQUENCE: 111
ccaccaagag gctagctaca acgacacgtc cac         33

<210> SEQ ID NO 112
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td42 DNAzyme against T-bet mRNA

<400> SEQUENCE: 112
gctggtccag gctagctaca acgacaagac cac         33

<210> SEQ ID NO 113
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td43 DNAzyme against T-bet mRNA

<400> SEQUENCE: 113
gctctggtag gctagctaca acgacgccag tgg         33

<210> SEQ ID NO 114
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td44 DNAzyme against T-bet mRNA

<400> SEQUENCE: 114
ctgcacccag gctagctaca acgattgccg ctc         33

<210> SEQ ID NO 115
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td45 DNAzyme against T-bet mRNA

<400> SEQUENCE: 115
cacactgcag gctagctaca acgaccactt gcc         33

<210> SEQ ID NO 116
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td46 DNAzyme against T-bet mRNA

<400> SEQUENCE: 116
ctttccacag gctagctaca acgatgcacc cac         33

<210> SEQ ID NO 117
<211> LENGTH: 33
<212> TYPE: DNA

<213> ORGANISM: Homo sapiens
<220> FEATURE:
<221> NAME/KEY: misc_feature
<222> LOCATION: (1)..(33)
<223> OTHER INFORMATION: td47 DNAzyme against T-bet mRNA

<400> SEQUENCE: 117
gcctttccag gctagctaca acgaactgca ccc                33

<210> SEQ ID NO 118
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td48 DNAzyme against T-bet mRNA

<400> SEQUENCE: 118
ttcctggcag gctagctaca acgagctgcc ctc                33

<210> SEQ ID NO 119
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td49 DNAzyme against T-bet mRNA

<400> SEQUENCE: 119
gtggacgtag gctagctaca acgaaggcgg ttt                33

<210> SEQ ID NO 120
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td50 DNAzyme against T-bet mRNA

<400> SEQUENCE: 120
ccgggtggag gctagctaca acgagtacag gcg                33

<210> SEQ ID NO 121
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td51 DNAzyme against T-bet mRNA

<400> SEQUENCE: 121
cctggcgcag gctagctaca acgaccagtg cgc                33

<210> SEQ ID NO 122
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td52 DNAzyme against T-bet mRNA

<400> SEQUENCE: 122
caaatgaaag gctagctaca acgattcctg gcg                33

-continued

```
<210> SEQ ID NO 123
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td53 DNAzyme against T-bet mRNA

<400> SEQUENCE: 123
tttcccaaag gctagctaca acgagaaact tcc                                      33

<210> SEQ ID NO 124
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td54 DNAzyme against T-bet mRNA

<400> SEQUENCE: 124
attgttggag gctagctaca acgagccccc ttg                                      33

<210> SEQ ID NO 125
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td55 DNAzyme against T-bet mRNA

<400> SEQUENCE: 125
tgggtcacag gctagctaca acgatgttgg acg                                      33

<210> SEQ ID NO 126
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td56 DNAzyme against T-bet mRNA

<400> SEQUENCE: 126
tctgggtcag gctagctaca acgaattgtt gga                                      33

<210> SEQ ID NO 127
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td57 DNAzyme against T-bet mRNA

<400> SEQUENCE: 127
gcacaatcag gctagctaca acgactgggt cac                                      33

<210> SEQ ID NO 128
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td58 DNAzyme against T-bet mRNA
```

```
<400> SEQUENCE: 128
ggagcacaag gctagctaca acgacatctg ggt                               33

<210> SEQ ID NO 129
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td59 DNAzyme against T-bet mRNA

<400> SEQUENCE: 129
actggagcag gctagctaca acgaaatcat ctg                               33

<210> SEQ ID NO 130
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td60 DNAzyme against T-bet mRNA

<400> SEQUENCE: 130
atggagggag gctagctaca acgatggagc aca                               33

<210> SEQ ID NO 131
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td61 DNAzyme against T-bet mRNA

<400> SEQUENCE: 131
tggtacttag gctagctaca acgaggaggg act                               33

<210> SEQ ID NO 132
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td62 DNAzyme against T-bet mRNA

<400> SEQUENCE: 132
gggctggtag gctagctaca acgattatgg agg                               33

<210> SEQ ID NO 133
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td63 DNAzyme against T-bet mRNA

<400> SEQUENCE: 133
tcaacgatag gctagctaca acgagcagcc ggg                               33

<210> SEQ ID NO 134
<211> LENGTH: 33
<212> TYPE: DNA
<213> ORGANISM: Homo sapiens
<220> FEATURE:
```

```
<221> NAME/KEY: misc_feature
<222> LOCATION: (1)..(33)
<223> OTHER INFORMATION: td64 DNAzyme against T-bet mRNA

<400> SEQUENCE: 134
cctcaacgag gctagctaca acgaatgcag ccg                              33

<210> SEQ ID NO 135
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td65 DNAzyme against T-bet mRNA

<400> SEQUENCE: 135
tcacctcaag gctagctaca acgagatatg cag                              33

<210> SEQ ID NO 136
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td66 DNAzyme against T-bet mRNA

<400> SEQUENCE: 136
cgtcgttcag gctagctaca acgactcaac gat                              33

<210> SEQ ID NO 137
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td67 DNAzyme against T-bet mRNA

<400> SEQUENCE: 137
gtaaagatag gctagctaca acgagcgtgt tgg                              33

<210> SEQ ID NO 138
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td68 DNAzyme against T-bet mRNA

<400> SEQUENCE: 138
aagtaaagag gctagctaca acgaatgcgt gtt                              33

<210> SEQ ID NO 139
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td69 DNAzyme against T-bet mRNA

<400> SEQUENCE: 139
ggcaatgaag gctagctaca acgatgggtt tct                              33

<210> SEQ ID NO 140
```

```
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td70 DNAzyme against T-bet mRNA

<400> SEQUENCE: 140
tcacggcaag gctagctaca acgagaactg ggt                                    33

<210> SEQ ID NO 141
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td71 DNAzyme against T-bet mRNA

<400> SEQUENCE: 141
aggcagtcag gctagctaca acgaggcaat gaa                                    33

<210> SEQ ID NO 142
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td72 DNAzyme against T-bet mRNA

<400> SEQUENCE: 142
atctcggcag gctagctaca acgatctggt agg                                    33

<210> SEQ ID NO 143
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td73 DNAzyme against T-bet mRNA

<400> SEQUENCE: 143
gctgagtaag gctagctaca acgactcggc att                                    33

<210> SEQ ID NO 144
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td74 DNAzyme against T-bet mRNA

<400> SEQUENCE: 144
tattatcaag gctagctaca acgatttcag ctg                                    33

<210> SEQ ID NO 145
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td75 DNAzyme against T-bet mRNA

<400> SEQUENCE: 145
```

| | |
|---|---|
| gggttattag gctagctaca acgacaattt tca | 33 |

<210> SEQ ID NO 146
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td76 DNAzyme against T-bet mRNA

<400> SEQUENCE: 146

| | |
|---|---|
| aaggggttag gctagctaca acgatatcaa ttt | 33 |

<210> SEQ ID NO 147
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td77 DNAzyme against T-bet mRNA

<400> SEQUENCE: 147

| | |
|---|---|
| ctcccggaag gctagctaca acgacctttg gca | 33 |

<210> SEQ ID NO 148
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td78 DNAzyme against T-bet mRNA

<400> SEQUENCE: 148

| | |
|---|---|
| gtacatggag gctagctaca acgatcaaag ttc | 33 |

<210> SEQ ID NO 149
<211> LENGTH: 2588
<212> TYPE: DNA
<213> ORGANISM: Homo sapiens
<220> FEATURE:
<221> NAME/KEY: td54 bindingsite
<222> LOCATION: (952)..(970)
<220> FEATURE:
<221> NAME/KEY: td69 bindingsite
<222> LOCATION: (1096)..(1114)
<220> FEATURE:
<221> NAME/KEY: td70 bindingsite
<222> LOCATION: (1100)..(1118)

<400> SEQUENCE: 149

| | |
|---|---|
| cggcccgctg gagaggaagc ccgagagctg ccgcgcgcct gccggacgag ggcgtagaag | 60 |
| ccaggcgtca gagcccgggc tccggtgggg tccccaccc ggccctcggg tccccgccc | 120 |
| cctgctccct gcccatccca gcccacgcga ccctctcgcg cgcggagggg cgggtcctcg | 180 |
| acggctacgg gaaggtgcca gcccgccccg gatgggcatc gtggagccgg gttgcggaga | 240 |
| catgctgacg ggcaccgagc cgatgccggg gagcgacgag ggccgggcgc ctggcgccga | 300 |
| cccgcagcac cgctacttct acccggagcc gggcgcgcag gacgcggacg agcgtcgcgg | 360 |
| gggcggcagc ctgggtctc cctacccggg gggcgccttg gtgcccgccc cgccgagccg | 420 |
| cttccttgga gcctacgcct acccgcgcg accccaggcg gccggcttcc ccggcgcggg | 480 |
| cgagtccttc ccgccgccg cggacgccga ggctaccag ccgggcgagg gctacgccgc | 540 |
| cccggacccg cgcgccgggc tctacccggg gccgcgtgag gactacgcgc tacccgcggg | 600 |

```
actggaggtg tcggggaaac tgagggtcgc gctcaacaac cacctgttgt ggtccaagtt    660
taatcagcac cagacagaga tgatcatcac caagcaggga cggcggatgt tcccattcct    720
gtcatttact gtggccgggc tggagcccac cagccactac aggatgtttg tggacgtggt    780
cttggtggac cagcaccact ggcggtacca gagcggcaag tgggtgcagt gtggaaaggc    840
cgagggcagc atgccaggaa accgcctgta cgtccacccg gactccccca acacaggagc    900
gcactggatg cgccaggaag tttcatttgg gaaactaaag ctcacaaaca caagggggc    960 gtccaacaat gtgacccaga tgattgtgct ccagtccctc cataagtacc agccccggct   1020
gcatatcgtt gaggtgaacg acggagagcc agaggcagcc tgcaacgctt ccaacacgca   1080
tatctttact ttccaagaaa cccagttcat tgccgtgact gcctaccaga atgccgagat   1140
tactcagctg aaaattgata taaccccctt tgccaaagga ttccgggaga ctttgagtc    1200 catgtacaca tctgttgaca ccagcatccc ctccccgcct ggaccaact gtcaattcct   1260 tgggggagat cactactctc ctctcctacc caaccagtat cctgttccca gccgcttcta   1320
ccccgacctt cctggccagg cgaaggatgt ggttccccag gcttactggc tgggggcccc   1380
ccgggaccac agctatgagg ctgagtttcg agcagtcagc atgaagcctg cattcttgcc   1440
ctctgcccct gggcccacca tgtcctacta ccgaggccag gaggtcctgg cacctggagc   1500
tggctggcct gtggcacccc agtaccctcc caagatgggc ccggccagct ggttccgccc   1560
tatgcggact ctgcccatgg aacccggccc tgaggctca gagggacggg gaccagagga   1620
ccagggtccc cccttggtgt ggactgagat tgccccatc cggccggaat ccagtgattc   1680
aggactgggc gaaggagact ctaagaggag gcgcgtgtcc ccctatcctt ccagtggtga   1740
cagctcctcc cctgctgggg ccccttctcc ttttgataag gaagctgaag acagtttta   1800 taactatttt cccaactgag cagatgacat gatgaaagga acagaaacag tgttattagg   1860
ttggaggaca ccgactaatt tgggaaacgg atgaaggact gagaaggccc ccgctccctc   1920
tggcccttct ctgtttagta gttggttggg gaagtggggc tcaagaagga ttttggggtt   1980
caccagatgc ttcctggccc acgatgaaac ctgagagggg tgtccccttg ccccatcctc   2040
tgccctaact acagtcgttt acctggtgct gcgtcttgct tttggtttcc agctggagaa   2100
aagaagacaa gaaagtcttg ggcatgaagg agctttttgc atctagtggg tggaggggt   2160 caggtgtggg acatgggagc aggagactcc actttcttcc tttgtacagt aactttcaac   2220
cttttcgttg gcatgtgtgt taatccctga tccaaaaaga acaaatacac gtatgttata   2280
accatcagcc cgccagggtc agggaaagga ctcacctgac tttggacagc tggcctgggc   2340
tccccctgct caaacacagt ggggatcaga gaaaagggc tggaaagggg gaatggccc    2400 acatctcaag aagcaagata ttgtttgtgg tggttgtgtg tgggtgtgtg тттттттcттт   2460

ттcттттcттт ttattttttt tgaatggggg aggctattta ttgtactgag agtggtgtct   2520
ggatatattc cttttgtctt catcactttc tgaaataaac ataaaactgt taaaaaaaaa   2580
aaaaaaaa                                                           2588
```

<210> SEQ ID NO 150
<211> LENGTH: 2450
<212> TYPE: DNA
<213> ORGANISM: Homo sapiens
<220> FEATURE:
<221> NAME/KEY: mutation
<222> LOCATION: (134)..(134)
<220> FEATURE:
<221> NAME/KEY: mutation
<222> LOCATION: (310)..(310)

```
<220> FEATURE:
<221> NAME/KEY: td54 bindingsite
<222> LOCATION: (952)..(970)
<220> FEATURE:
<221> NAME/KEY: td69 bindingsite
<222> LOCATION: (1096)..(1114)
<220> FEATURE:
<221> NAME/KEY: td70 bindingsite
<222> LOCATION: (1100)..(1118)
<220> FEATURE:
<221> NAME/KEY: mutation
<222> LOCATION: (1399)..(1399)
<220> FEATURE:
<221> NAME/KEY: mutation
<222> LOCATION: (1556)..(1556)

<400> SEQUENCE: 150
cggcccgctg gagaggaagc ccgagagctg ccgcgcgcct gccggacgag ggcgtagaag      60
ccaggcgtca gagcccgggc tccggtgggg tcccccaccc ggccctcggg tccccgccc     120 cctgctccct gcctatccca gcccacgcga ccctctcgcg cgcggagggg cgggtcctcg     180
acggctacgg gaaggtgcca gcccgccccg gatgggcatc gtggagccgg gttgcggaga     240
catgctgacg ggcaccgagc cgatgccggg gagcgacgag ggccgggcgc ctggcgccga     300
cccgcagcag cgctacttct acccggagcc gggcgcgcag gacgcggacg agcgtcgcgg     360
gggcggcagc ctggggtctc cctacccggg gggcgcttg gtgcccgccc cgccgagccg     420
cttccttgga gcctacgcct acccgccgcg accccaggcg gccggcttcc ccggcgcggg     480
cgagtccttc ccgccgcccg cggacgccga gggctaccag ccgggcgagg gctacgccgc     540
cccggacccg cgcgccgggc tctacccggg gccgcgtgag gactacgcgc tacccgcggg     600
actggaggtg tcggggaaac tgaggtcgc gctcaacaac cacctgttgt ggtccaagtt     660
taatcagcac cagacagaga tgatcatcac caagcaggga cggcggatgt tcccattcct     720
gtcatttact gtggccgggc tggagcccac cagccactac aggatgtttg tggacgtggt     780
cttggtggac cagcaccact ggcggtacca gagcggcaag tgggtgcagt gtggaaaggc     840
cgagggcagc atgccaggaa accgcctgta cgtccacccg gactccccca acacaggagc     900
gcactggatg cgccaggaag tttcatttgg gaaactaaag ctcacaaaca caagggggc     960 gtccaacaat gtgacccaga tgattgtgct ccagtccctc cataagtacc agccccggct    1020
gcatatcgtt gaggtgaacg acggagagcc agaggcagcc tgcaacgctt ccaacacgca    1080
tatctttact ttccaagaaa cccagttcat tgccgtgact gcctaccaga atgccgagat    1140
tactcagctg aaaattgata taacccctt tgccaaagga ttccgggaga actttgagtc    1200
catgtacaca tctgttgaca ccagcatccc ctccccgcct ggacccaact gtcaattcct    1260
tgggggagat cactactctc ctctcctacc caaccagtat cctgttccca gccgcttcta    1320
ccccgacctt cctggccagg cgaaggatgt ggttccccag gcttactggc tgggggcccc    1380
ccgggaccac agctatgggg ctgagtttcg agcagtcagc atgaagcctg cattcttgcc    1440
ctctgcccct gggcccacca tgtcctacta ccgaggccag gaggtcctgg cacctggagc    1500
tggctggcct gtggcacccc agtaccctcc caagatgggc ccggccagct ggttcagccc    1560
tatgcggact ctgcccatgg aacccggccc tggaggctca gagggacggg gaccagagga    1620
ccagggtccc cccttggtgt ggactgagat tgccccatc cggccggaat ccagtgattc    1680
aggactgggc gaaggagact ctaagaggag cgcgcgtgtcc ccctatcctt ccagtggtga    1740
cagctcctcc cctgctgggg ccccttctcc ttttgataag gaagctgaag acagttttta    1800
taactatttt cccaactgag cagatgacat gatgaaagga acagaaacag tgttattagg    1860
```

```
ttggaggaca ccgactaatt tgggaaacgg atgaaggact gagaaggccc ccgctccctc   1920
tggcccttct ctgtttagta gttggttggg gaagtggggc tcaagaagga ttttgggggtt   1980 caccagatgc ttcctggccc acgatgaaac ctgagagggg tgtccccttg ccccatcctc   2040
tgccctaact acagtcgttt acctggtgct gcgtcttgct tttggtttcc agctggagaa   2100
aagaagacaa gaaagtcttg ggcatgaagg agcttttgc atctagtggg tgggaggggt   2160
caggtgtggg acatgggagc aggagactcc actttcttcc tttgtacagt aactttcaac   2220
cttttcgttg gcatgtgtgt taatccctga tccaaaaaga acaaatacac gtatgttata   2280
accatcagcc cgccagggtc agggaaagga ctcacctgac tttggacagc tggcctgggc   2340 tcccctgct caaacacagt ggggatcaga gaaaggggc tggaagggg gaatggccc   2400 acatctcaag aagcaagata ttgtttgtgg tggttgtgtg tgggtgtgtg               2450

<210> SEQ ID NO 151
<211> LENGTH: 2399
<212> TYPE: DNA
<213> ORGANISM: Homo sapiens

<400> SEQUENCE: 151
ggcgccgtct tgatactttc agaaagaatg cattccctgt aaaaaaaaaa aaaaaatact     60
gagagaggga gagagagaga gaagaagaga gagagacgga gggagagcga gacagagcga    120
gcaacgcaat ctgaccgagc aggtcgtacg ccgccgcctc ctcctcctct ctgctcttcg    180
ctacccaggt gacccgagga gggactccgc ctccgagcgg ctgaggaccc cggtgcagag    240
gagcctggct cgcagaattg cagagtcgtc gccccttttt acaacctggt cccgttttat    300
tctgccgtac ccagttttg gatttttgtc ttccccttct tctctttgct aaacgacccc     360
tccaagataa ttttaaaaa accttctcct ttgctcacct ttgcttccca gccttcccat    420
cccccccacg aaagcaaatc attcaacgac ccccgaccct ccgacggcag gagccccccg    480
acctcccagg cggaccgccc tccctccccg cgcgcgggtt ccgggcccgg cgagagggcg    540
cgagcacagc cgaggccatg gaggtgacgg cggaccagcc gcgctgggtg agccaccacc    600 acccccgccgt gctcaacggg cagcacccgg acacgcacca cccgggcctc agccactcct    660
acatggacgc ggcgcagtac ccgctgccgg aggaggtgga tgtgcttttt aacatcgacg    720
gtcaaggcaa ccacgtcccg ccctactacg gaaactcggt cagggccacg gtgcagaggt    780
accctccgac ccaccacggg agccaggtgt gccgcccgcc tctgcttcat ggatccctac    840
cctggctgga cggcggcaaa gccctgggca gccaccacac cgcctccccc tggaatctca    900
gccccttctc caagacgtcc atccaccacg gctcccgggg gccctctcc gtctaccccc    960 cggcctcgtc ctcctccttg tcgggggggcc acgccagccc gcacctcttc accttcccgc   1020
ccaccccgcc gaaggacgtc tccccggacc catcgctgtc caccccaggc tcggccggct   1080
cggcccggca ggacgagaaa gagtgcctca agtaccaggt gccccctgccc gacagcatga   1140 agctggagtc gtcccactcc cgtggcagca tgaccgccct gggtggagcc tcctcgtcga   1200
cccaccaccc catcaccacc taccgcccct acgtgcccga gtacagctcc ggactcttcc   1260
cccccagcag cctgctgggc ggctcccca ccggcttcgg atgcaagtcc aggcccaagg   1320
cccggtccag cacagaaggc agggagtgtg tgaactgtgg gcaacctcg accccactgt   1380 ggcggcgaga tggcacggga cactacctgt gcaacgcctg cgggctctat cacaaaatga   1440
acggacagaa ccggccctc attaagccca gcgaaggct gtctgcagcc aggagagcag   1500
ggacgtcctg tgcgaactgt cagaccacca caaccacact ctggaggagg aatgccaatg   1560
```

```
gggaccctgt ctgcaatgcc tgtgggctct actacaagct tcacaatatt aacagacccc    1620
tgactatgaa gaaggaaggc atccagacca gaaaccgaaa aatgtctagc aaatccaaaa    1680
agtgcaaaaa agtgcatgac tcactggagg acttccccaa gaacagctcg tttaacccgg    1740
ccgccctctc cagacacatg tcctccctga gccacatctc gcccttcagc cactccagcc    1800
acatgctgac cacgcccacg ccgatgcacc cgccatccag cctgtccttt ggaccacacc    1860 accccctccag catggtcacc gccatgggtt agagccctgc tcgatgctca cagggccccc    1920
agcgagagtc cctgcagtcc ctttcgactt gcattttgc aggagcagta tcatgaagcc    1980
taaacgcgat ggatatatgt ttttgaaggc agaaagcaaa attatgtttg ccactttgca    2040
aaggagctca ctgtggtgtc tgtgttccaa ccactgaatc tggaccccat ctgtgaataa    2100
gccattctga ctcatatccc ctatttaaca gggtctctag tgctgtgaaa aaaaaaatgc    2160
tgaacattgc atataactta tattgtaaga aatactgtac aatgacttta ttgcatctgg    2220
gtagctgtaa ggcatgaagg atgccaagaa gtttaaggaa tatgggagaa atagtgtgga    2280
aattaagaag aaactaggtc tgatattcaa atggacaaac tgccagtttt gtttcctttc    2340
actggccaca gttgtttgat gcattaaaag aaaataaaaa aagaaaaaa gagaaaaga    2399

<210> SEQ ID NO 152
<211> LENGTH: 2365
<212> TYPE: DNA
<213> ORGANISM: Homo sapiens

<400> SEQUENCE: 152
tcccagcctt cccatccccc caccgaaagc aaatcattca acgaccccg accctccgac      60 ggcaggagcc ccccgacctc ccaggcggac cgcccttccc tccccgcgcg ggttccgggc    120
ccggcgagag ggcgcgacga cagccgaggc catggaggtg acgcggacc agccgcgctg    180 ggtgagccac caccaccccg ccgtgctcaa cgggcagcac ccggacacgc accacccggg    240
cctcagccac tcctacatgg acgcggcgca gtacccgctg ccggaggagg tggatgtgct    300
ttttaacatc gacggtcaag gcaaccacgt cccgccctac tacggaaact cggtcagggc    360
cacggtgcag aggtaccctc cgaccccacca cgggagccag gtgtgccgcc cgcctctgct    420
tcatggatcc ctaccctggc tggacggcgg caaagccctg ggcagccacc acaccgcctc    480
cccctggaat ctcagcccct tctccaagac gtccatccac cacggctccc cggggccccct    540 ctccgtctac cccccggcct cgtcctcctc cttgtcgggg ggccacgcca gccgcacct    600 cttcaccttc ccgcccaccc cgccgaagga cgtctcccg gacccatcgc tgtccaccc    660 aggctcggcc ggctcggccc ggcaggacga gaaagagtgc tcaagtacc aggtgcccct    720 gcccgacagc atgaagctgg agtcgtccca ctccgtggc agcatgaccg ccctgggtgg    780
agcctcctcg tcgacccacc accccatcac cacctacccg ccctacgtgc cgagtacag    840 ctccggactc ttccccccca gcagcctgct gggcggctcc cccaccggct cggatgcaa    900 gtccaggccc aaggcccggt ccagcacagg cagggagtgt gtgaactgtg ggcaacctc    960 gacccactg tggcggcgag atggcacggg acactacctg tgcaacgcct gcgggctcta    1020
tcacaaaatg aacggacaga accggcccct cattaagccc aagcgaaggc tgtctgcagc    1080
caggagagca gggacgtcct gtgcgaactg tcagaccacc acaaccacac tctggaggag    1140
gaatgccaat ggggaccctg tctgcaatgc ctgtgggctc tactacaagc ttcacaatat    1200
taacagaccc ctgactatga agaaggaagg catccagacc agaaaccgaa aatgtctag    1260 caaatccaaa aagtgcaaaa aagtgcatga ctcactggag gacttcccca agaacagctc    1320
```

-continued

```
gtttaacccg gccgccctct ccagacacat gtcctccctg agccacatct cgcccttcag    1380
ccactccagc cacatgctga ccacgccacc gccgatgcac ccgccatcca gcctgtcctt    1440
tggaccacac caccccctcca gcatggtcac cgccatgggt tagagccctg ctcgatgctc   1500
acagggcccc cagcgagagt ccctgcagtc cctttcgact tgcatttttg caggagcagt    1560
atcatgaagc ctaaacgcga tggatatatg ttttttgaagg cagaaagcaa aattatgttt   1620
gccactttgc aaaggagctc actgtggtgt ctgtgttcca accactgaat ctggaccccca   1680 tctgtgaata agccattctg actcatatcc cctatttaac agggtctcta gtgctgtgaa    1740
aaaaaaaaat cctgaacatt gcatataact tatattgtaa gaaatactgt acaatgactt    1800
tattgcatct gggtagctgt aaggcatgaa ggatgccaag aagtttaagg aatatgggag    1860
aaatagtgtg gaaattaaga agaaactagg tctgatattc aaatggacaa actgccagtt    1920
ttgtttcctt tcactggcca cagttgtttg atgcattaaa agaaataaa aaaaagaaaa      1980 aagagaaaag aaaaaaaaag aaaaaagttg taggcgaatc atttgttcaa agctgttggc    2040
cctctgcaaa ggaaatacca gttctgggca atcagtgtta ccgttcacca gttgccattg    2100
agggtttcag agagccttttt tctaggccta catgctttgt gaacaagtcc ctgtaattgt    2160
tgtttgtatg tataattcaa agcaccaaaa taagaaaaga tgtagattta tttcatcata    2220
ttatacagac cgaactgttg tataaattta tttactgcta gtcttaagaa ctgctttctt    2280
tcgtttgttt gtttcaatat tttccttctc tctcaatttt cggttgaata aactagatta    2340
cattcagttg gcaaaaaaaa aaaaa                                          2365

<210> SEQ ID NO 153
<211> LENGTH: 2728
<212> TYPE: DNA
<213> ORGANISM: Homo sapiens
<220> FEATURE:
<221> NAME/KEY: mutation
<222> LOCATION: (57)..(57)
<220> FEATURE:
<221> NAME/KEY: mutation
<222> LOCATION: (59)..(59)
<220> FEATURE:
<221> NAME/KEY: mutation
<222> LOCATION: (69)..(69)
<220> FEATURE:
<221> NAME/KEY: hgd40 bindingsite
<222> LOCATION: (909)..(927)

<400> SEQUENCE: 153
ggcgccgtct tgatactttc agaaagaatg cattccctgt aaaaaaaaaa aaaaaaaat     60 actgagagag ggagagagag agaagaagag agagagacgg agggagagcg agacagagcg    120
agcaacgcaa tctgaccgag caggtcgtac gccgccgcct cctcctcctc tctgctcttc    180
gctacccagg tgacccgagg agggactccg cctccgagcg gctgaggacc ccggtgcaga    240
ggagcctggc tcgcagaatt gcagagtcgt cgccccttttt tacaacctgg tcccgttttta   300 ttctgccata cccagttttt ggatttttgt cttccccttc ttctctttgc taaacgaccc    360
ctccaagata attttttaaaa aaccttctcc tttgctcacc tttgcttccc agccttccca    420 tcccccacc gaaagcaaat cattcaacga ccccgaccc tccgacggca ggagccccc      480 gacctcccag gcggaccgcc ctccctcccc gcgcgcgggt tccgggcccg gcgagagggc    540
gcgagcacag ccgaggccat ggaggtgacg gcggaccagc cgcgctgggt gagccaccac    600
caccccgccg tgctcaacgg gcagcacccg gacacgcacc acccgggcct cagccactcc    660
tacatggacg cggcgcagta cccgctgccg gaggaggtgg atgtgctttt taacatcgac    720
```

```
ggtcaaggca accacgtccc gccctactac ggaaactcgg tcagggccac ggtgcagagg    780
taccctccga cccaccacgg gagccaggtg tgccgcccgc ctctgcttca tggatccctc    840
cctggctgga cggcggcaaa gccctgggca gccaccacac cgcctccccc tggaatctca    900 gcccttctc caagacgtcc atccaccacg gctcccggg gccctctcc gtctaccccc       960 cggcctcgtc ctcctccttg tcggggggcc acgccagccc gcacctcttc accttcccgc   1020
ccaccccgcc gaaggacgtc tccccggacc catcgctgtc caccccaggc tcggccggct   1080
cggcccggca ggacgagaaa gagtgcctca agtaccaggt gcccctgccc gacagcatga   1140
agctggagtc gtcccactcc cgtggcagca tgaccgccct gggtggagcc tcctcgtcga   1200
cccaccaccc catcaccacc tacccgccct acgtgcccga gtacagctcc ggactcttcc   1260
cccccagcag cctgctgggc ggctccccca ccggcttcgg atgcaagtcc aggcccaagg   1320
cccggtccag cacagaaggc agggagtgtg tgaactgtgg gcaacctcg accccactgt    1380 ggcggcgaga tggcacggga cactacctgt gcaacgcctg cgggctctat cacaaaatga   1440
acggacagaa ccggcccctc attaagccca gcgaaggct gtctgcagcc aggagagcag    1500
ggacgtcctg tgcgaactgt cagaccacca caaccacact ctggaggagg aatgccaatg   1560
gggaccctgt ctgcaatgcc tgtgggctct actacaagct tcacaatatt aacagacccc   1620
tgactatgaa gaaggaaggc atccagacca gaaaccgaaa aatgtctagc aaatccaaaa   1680
agtgcaaaaa agtgcatgac tcactggagg acttccccaa gaacagctcg tttaacccgg   1740
ccgccctctc cagacacatg tcctccctga gccacatctc gcccttcagc caccccagcc   1800
acatgctgac cacgcccacg ccgatgcacc cgccatccag cctgtccttt ggaccacacc   1860
acccctccag catggtcacc gccatgggtt agagccctgc tgatgctcac agggccccca   1920
gcgagagtcc ctgcagtccc tttcgacttg cattttttgca ggagcagtat catgaagcct   1980
aaacgcgatg gatatatgtt tttgaaggca gaaagcaaaa ttatgcttgc cactttgcaa   2040
aggagctcac tgtggtgtct gtgttccaac cactgaatct ggaccccatc tgtgaataag   2100
ccattctgac tcatatcccc tatttaacag ggtctctagt gctgtgaaaa aaaaaaatgc   2160
tgaacattgc atataactta tattgtaaga atactgtac aatgacttta ttgcatctgg    2220
gtagctgtaa ggcatgaagg atgccaagaa gtttaaggaa tatgggagaa atagtgtgga   2280
aattaagaag aaactaggtc tgatattcaa atggacaaac tgccagtttt gtttcctttc   2340
actggccaca gttgtttgat gcattaaaag aaaataaaaa aagaaaaag agaaaagaaa    2400 aaaaagaaa aagttgtag gcgaatcatt tgttcaaagc tgttggcctc tgcaaaggaa    2460
ataccagttc gggcaatcag tgttaccgtt caccagttgc cattgagggt ttcagagagc   2520
ctttttctag gcctacatgc tttgtgaaca agtccctgta attgttgttt gtatgtataa   2580
ttcaaagcac caaaataaga aaagatgtag atttatttca tcatattata cagaccgaac   2640
tgttgtataa atttatttac tgctagtctt aagaactgct ttctttcgtt tgtttgtttc   2700
aatattttcc ttctctctca attttcgg                                      2728
```

<210> SEQ ID NO 154
<211> LENGTH: 15
<212> TYPE: DNA

```
<213> ORGANISM: artificial sequence
<220> FEATURE:
<221> NAME/KEY: misc_feature
<222> LOCATION: (1)..(15)
<223> OTHER INFORMATION: Catalytic Domain of DNAzyme against GATA-3mRNA

<400> SEQUENCE: 154
ggctagctac aacga                                                15
```

The invention claimed is:

1. A DNAzyme which binds to GATA-3 mRNA and functionally inactivates it, which comprises:
   a catalytic domain with the nucleotide sequence GGCTAGCTACAACGA SEQ ID NO: 154 or a modified sequence with comparable biological effect, which cleaves the GATA-3 mRNA at every purine:pyrimidine binding site to which it is bonded,
   a right substrate binding domain adjoining the 3' end of the catalytic domain having polynucleotide sequence GTCTTGGAG and
   a left substrate binding domain adjoining the 5' end of the catalytic domain having polynucleotide sequence GTGGATGGA, both substrate binding domains being respectively complementary to two regions of the GATA 3 mRNA so that they hybridize with the mRNA, and which is active in vivo.

2. A DNAzyme according to claim 1, which comprises the sequence hgd 40 GTGGATGGA GGCTAGCTACAACGA GTCTTGGAG SEQ ID NO: 40.

3. A DNAzyme according to claim 1 which cleaves the catalytic domain of the GATA-3 mRNA at every purine:uracil binding site.

4. A DNAzyme according to claim 1 which is stabilized against decomposition within the organism by introduction of a 3'-3' inversion.

5. A DNAzyme according to claim 1 which is stabilized against decomposition within the organism by introduction of modified nucleotides or nucleotide compounds.

6. A DNAzyme according to claim 1 which includes an inverse thymidine on the 3' end and/or a FAM label on the 5' end.

7. A medicament containing a DNAzyme according to claim 1 and a pharmaceutically acceptable carrier.

* * * * *